(12) United States Patent
Bi et al.

(10) Patent No.: US 6,511,810 B2
(45) Date of Patent: Jan. 28, 2003

(54) POLYNUCLEOTIDE SEQUENCE ASSAY

(75) Inventors: Wanli Bi, San Ramon, CA (US); Kenneth J. Livak, San Jose, CA (US); Will Bloch, White Salmon, WA (US)

(73) Assignee: Applera Corporation, Foster City, CA (US)

( * ) Notice: Subject to any disclaimer, the term of this patent is extended or adjusted under 35 U.S.C. 154(b) by 0 days.

(21) Appl. No.: 09/898,323

(22) Filed: Jul. 3, 2001

(65) Prior Publication Data

US 2002/0150904 A1 Oct. 17, 2002

Related U.S. Application Data

(60) Provisional application No. 60/216,514, filed on Jul. 3, 2000.

(51) Int. Cl.⁷ ............................ C12Q 1/68; C07H 21/02; C07H 21/04
(52) U.S. Cl. ............................ 435/6; 536/23.1; 536/24.3
(58) Field of Search ............................ 435/6; 536/23.1, 536/24.3

(56) References Cited

U.S. PATENT DOCUMENTS

| | | | | |
|---|---|---|---|---|
| 4,988,617 A | * | 1/1991 | Lundegren et al. ............ | 435/6 |
| 5,494,810 A | * | 2/1996 | Barany et al. ............ | 435/91.52 |
| 5,516,663 A | | 5/1996 | Backman et al. | |
| 5,573,907 A | | 11/1996 | Carrino et al. | |
| 5,792,607 A | | 8/1998 | Backman et al. | |
| 5,846,717 A | | 12/1998 | Brow et al. | |
| 5,985,557 A | | 11/1999 | Prudent et al. | |
| 5,994,069 A | | 11/1999 | Hall et al. | |
| 6,090,543 A | | 7/2000 | Prudent et al. | |
| 6,232,075 B1 | * | 5/2001 | Williams ........................ | 435/6 |
| 6,268,148 B1 | * | 7/2001 | Barany et al. .................. | 435/6 |
| 6,312,892 B1 | * | 11/2001 | Barany et al. .................. | 435/6 |
| 6,368,803 B1 | * | 4/2002 | Western et al. ................ | 435/6 |

FOREIGN PATENT DOCUMENTS

| | | |
|---|---|---|
| WO | WO 97/27214 A1 | 7/1997 |
| WO | WO 98/23774 A1 | 6/1998 |
| WO | WO 98/42873 A1 | 10/1998 |

OTHER PUBLICATIONS

Nickerson et al., PNAS 87 : 8923–8927 (1990).*
Wu et al., Genomics 4 : 560–569 (1989).*
Matthews et al., Analytical Biochemistry 169 : 1–25 (1988).*
Reyes et al., Clinical Chemistry 43 (1) : 40–44 (1997).*
Barany, "The Ligase Chain Reaction in a PCR World," *PCR Methods and Application*, vol. 1, No. 1, pp. 5–16, Aug. 1991.
Griffin et al., "Direct genetic analysis by matrix–assisted laser desorption/ionization mass spectrometry," *Proc. Natl. Acad. Sci.*, vol. 96, pp. 6301–6306, May 1999.
Kaiser et al., "A Comparison of Eubacterial and Archaeal Structure–specific 5'Exonucleases," *The Journal of Biological Chemistry*, vol. 274, No. 30, pp. 21387–21394, Jul. 23, 1999.
Lundquist et al., "Transient Generation of Displaced Single–Stranded DNA during Nick Translation," *Cell*, vol. 31, pp. 53–60, Nov. 1982.
Lyamichev et al., "Comparison of the 5' nuclease activities of Taq DNA polymerase and its isolated nuclease domain," *Proc. Natl. Acad. Sci.*, vol. 96, pp. 6143–6148, May 1999.
Lyamichev et al., "Polymorphism identification and quantitative detection of genomic DNA by invasive cleavage of oligonucleotide probes," *Nature Biotechnology*, vol. 17, pp. 292–296, Mar. 1999.
Ryan et al., "Non–PCR–Dependent Detection of the Factor V Leiden Mutation from Genomic DNA Using a Homogeneous Invader Microtiter Plate Assay," *Molecular Diagnostic*, vol. 4, No. 2, pp. 135–144, 1999.
Weidmann et al., Ligase Chain Reaction (LCR)–Overview and Applications, *PCR Methods and Application*, vol. 3, No. 4, pp. S51–S64, Feb. 1994.

* cited by examiner

*Primary Examiner*—Ethan C. Whisenant
(74) *Attorney, Agent, or Firm*—Vincent M. Powers

(57) ABSTRACT

Disclosed are methods for detecting or quantifying one or more target polynucleotide sequences in a sample. In one aspect, a sample is contacted with first and second probe pair that are capable of hybridizing to a selected target sequence and a corresponding complementary sequence, respectively. Probe cleavage and ligation results in the formation of ligation products which can be generated in an exponential fashion when the target sequence and/or complement are present in the sample. In another embodiment, a single probe pair can be used to form ligation product in a linear fashion from a complementary template. Reagents and kits are also disclosed.

158 Claims, No Drawings

SEQUENCE LISTING

<160> NUMBER OF SEQ ID NOS: 24

<210> SEQ ID NO 1
<211> LENGTH: 53
<212> TYPE: DNA
<213> ORGANISM: Homo sapiens

<400> SEQUENCE: 1
aagaaattat ctcggtcctc acaataaact gcgaggtcac tgtgagtttt cct          53

<210> SEQ ID NO 2
<211> LENGTH: 51
<212> TYPE: DNA
<213> ORGANISM: Homo sapiens

<400> SEQUENCE: 2
aaagcctcac agaggctgaa gtggcaacag agaaggaagg agaagacggg g            51

<210> SEQ ID NO 3
<211> LENGTH: 51
<212> TYPE: DNA
<213> ORGANISM: Homo sapiens

<400> SEQUENCE: 3
aaagcctcac agaggctgaa gtggccacag agaaggaagg agaagacggg g            51

<210> SEQ ID NO 4
<211> LENGTH: 29
<212> TYPE: DNA
<213> ORGANISM: Unknown
<220> FEATURE:
<223> OTHER INFORMATION: Ligation probe 1 for detecting SEQ ID NO:1

<400> SEQUENCE: 4
aagaaattat ctcggtcctc acaataaac                                     29

<210> SEQ ID NO 5
<211> LENGTH: 24
<212> TYPE: DNA
<213> ORGANISM: Unknown
<220> FEATURE:
<223> OTHER INFORMATION: Ligation probe 2 for detecting SEQ ID NO:1

<400> SEQUENCE: 5
actgcgaggt cactgtgagt tttc                                          24

<210> SEQ ID NO 6
<211> LENGTH: 25
<212> TYPE: DNA
<213> ORGANISM: Unknown
<220> FEATURE:
<223> OTHER INFORMATION: Ligation probe 3 for detecting SEQ ID NO:1

<400> SEQUENCE: 6
aagaaaactc acagtgacct cgcag                                         25

<210> SEQ ID NO 7
<211> LENGTH: 28
<212> TYPE: DNA
<213> ORGANISM: Unknown
<220> FEATURE:
<223> OTHER INFORMATION: Ligation probe 4 for detecting SEQ ID NO:1

<400> SEQUENCE: 7
agtttattgt gaggaccgag ataatttc                                      28

<210> SEQ ID NO 8
<211> LENGTH: 24
<212> TYPE: DNA
<213> ORGANISM: Unknown
<220> FEATURE:

<223> OTHER INFORMATION: Ligation probe 1 for detecting SEQ ID NO:2

<400> SEQUENCE: 8
aacctcacag aggctgaagt ggca                                    24

<210> SEQ ID NO 9
<211> LENGTH: 25
<212> TYPE: DNA
<213> ORGANISM: Unknown
<220> FEATURE:
<223> OTHER INFORMATION: Ligation probe 2 for detecting SEQ ID NO:2

<400> SEQUENCE: 9
aaacagagaa ggaaggagaa gacgg                                   25

<210> SEQ ID NO 10
<211> LENGTH: 26
<212> TYPE: DNA
<213> ORGANISM: Unknown
<220> FEATURE:
<223> OTHER INFORMATION: Ligation probe 3 for detecting SEQ ID NO:2

<400> SEQUENCE: 10
aaccgtcttc tccttccttc tctgtt                                  26

<210> SEQ ID NO 11
<211> LENGTH: 23
<212> TYPE: DNA
<213> ORGANISM: Unknown
<220> FEATURE:
<223> OTHER INFORMATION: Ligation probe 4 for detecting SEQ ID NO:2

<400> SEQUENCE: 11
atgccacttc agcctctgtg agg                                     23

<210> SEQ ID NO 12
<211> LENGTH: 24
<212> TYPE: DNA
<213> ORGANISM: Unknown
<220> FEATURE:
<223> OTHER INFORMATION: Ligation probe 1 for detecting SEQ ID NO:3

<400> SEQUENCE: 12
cccctcacag aggctgaagt ggcc                                    24

<210> SEQ ID NO 13
<211> LENGTH: 25
<212> TYPE: DNA
<213> ORGANISM: Unknown
<220> FEATURE:
<223> OTHER INFORMATION: Ligation probe 2 for detecting SEQ ID NO:3

<400> SEQUENCE: 13
acacagagaa ggaaggagaa gacgg                                   25

<210> SEQ ID NO 14
<211> LENGTH: 26
<212> TYPE: DNA
<213> ORGANISM: Unknown
<220> FEATURE:
<223> OTHER INFORMATION: Ligation probe 3 for detecting SEQ ID NO:3

<400> SEQUENCE: 14
ccccgtcttc tccttccttc tctgtg                                  26

```
<210> SEQ ID NO 15
<211> LENGTH: 23
<212> TYPE: DNA
<213> ORGANISM: Unknown
<220> FEATURE:
<223> OTHER INFORMATION: Ligation probe 4 for detecting SEQ ID NO:3

<400> SEQUENCE: 15
aggccacttc agcctctgtg agg                                              23

<210> SEQ ID NO 16
<211> LENGTH: 28
<212> TYPE: DNA
<213> ORGANISM: Unknown
<220> FEATURE:
<223> OTHER INFORMATION: Ligation probe P1 for detecting SEQ ID NO:1

<400> SEQUENCE: 16
aagaaattat ctcggtcctc acaataaa                                         28

<210> SEQ ID NO 17
<211> LENGTH: 51
<212> TYPE: DNA
<213> ORGANISM: Unknown
<220> FEATURE:
<223> OTHER INFORMATION: DNA segment containing SEQ ID NO:1

<400> SEQUENCE: 17
ttctttaata gagccaggag tgttatttga cgctccagtg acactcaaaa g               51

<210> SEQ ID NO 18
<211> LENGTH: 23
<212> TYPE: DNA
<213> ORGANISM: Unknown
<220> FEATURE:
<223> OTHER INFORMATION: Cleaved form of probe P2

<400> SEQUENCE: 18
ctgcgaggtc actgtgagtt ttc                                              23

<210> SEQ ID NO 19
<211> LENGTH: 51
<212> TYPE: DNA
<213> ORGANISM: Unknown
<220> FEATURE:
<223> OTHER INFORMATION: Ligation product of probes P1 and P2 from
      Scheme Ib, following cleavage of P2

<400> SEQUENCE: 19
aagaaattat ctcggtcctc acaataaact gcgaggtcac tgtgagtttt c               51

<210> SEQ ID NO 20
<211> LENGTH: 51
<212> TYPE: DNA
<213> ORGANISM: Unknown
<220> FEATURE:
<223> OTHER INFORMATION: Complement of SEQ ID NO:2

<400> SEQUENCE: 20
tttcggagtg tctccgactt caccgttgtc tcttccttcc tcttctgccc c               51

<210> SEQ ID NO 21
<211> LENGTH: 23
<212> TYPE: DNA
<213> ORGANISM: Unknown
<220> FEATURE:
<223> OTHER INFORMATION: Cleaved form of probe Ap2 from Scheme IIa
```

```
<400> SEQUENCE: 21
acagagaagg aaggagaaga cgg                                          23

<210> SEQ ID NO 22
<211> LENGTH: 21
<212> TYPE: DNA
<213> ORGANISM: Unknown
<220> FEATURE:
<223> OTHER INFORMATION: Cleaved form of probe Ap4 from Scheme IIa

<400> SEQUENCE: 22
ggagtgtctc cgacttcacc g                                            21

<210> SEQ ID NO 23
<211> LENGTH: 47
<212> TYPE: DNA
<213> ORGANISM: Unknown
<220> FEATURE:
<223> OTHER INFORMATION: Ligation product of probes Ap1 and Ap2 from
      Scheme IIb, following cleavage of Ap2

<400> SEQUENCE: 23
aacctcacag aggctgaagt ggcaacagag aaggaaggag aagacgg                47

<210> SEQ ID NO 24
<211> LENGTH: 47
<212> TYPE: DNA
<213> ORGANISM: Unknown
<220> FEATURE:
<223> OTHER INFORMATION: Ligation product of probes Ap3 and Ap4 from
      Scheme IIb, following cleavage of Ap4

<400> SEQUENCE: 24
ggagtgtctc cgacttcacc gttgtctctt ccttcctctt ctgccaa                47
```

POLYNUCLEOTIDE SEQUENCE ASSAY

This application claims the benefit of priority of U.S. provisional application Serial No. 60/216,514 filed Jul. 3, 2000, which is incorporated herein by reference.

FIELD OF THE INVENTION

The present invention relates to methods for detecting or quantifying one or more polynucleotide sequences in one or more samples, and to reagents and kits for use therein.

REFERENCES

Albretsen et al., *Anal. Biochem.* 189:40 (1990).
Ausubel et al., eds., *Current Protocols in Molecular Biology Vol.* 1, Chapter 2, Section I, John Wiley & Sons, New York (1993).
Barany et al., PCT Application No. PCT/US91/06103.
Barrett, R. W., et al., U.S. Pat. No. 5,482,867 (1996).
Beaucage and Iyer, *Tetrahedron* 48:2223–2311 (1992).
Bergot et al., PCT Application No. PCT/US90/05565 (WO 91/07507).
Boom et al., U.S. Pat. No. 5,234,809.
Brenner, PCT Publications No. WO 96/12014 and WO 96/41011.
Breslauer et al., *Proc. Natl. Acad. Sci.* 83:3746–3750 (1986).
Cantor et al, U.S. Pat. No. 5,482,836.
Dieffenbach et al., in *PCR Primer: A Laboratory Manual*, Dieffenbach and Dveksler, eds., pp. 133–142, CSHL Press, New York (1995).
Drmanac, R., et al., *Electrophoresis* 13:566 (1992).
Drmanac, R., et al., *Science* 260:1649 (1993).
Eckstein, F., *Oligonucleotides and Analogs: A Practical Approach*, Chapters 8 and 9, IRL Press, Oxford, GB (1991).
Fodor, S. P. A., et al., *Science* 251:767 (1991).
Fodor, S. P. A., et al., U.S. Pat. No. 5,445,934 (1995).
Fung et al, U.S. Pat. No. 4,757,141.
Gait, M. J., ed., *Oligonucleotide Synthesis: A Practical Approach*, IRL Press, Oxford, (1984 and 1990 editions).
Grossman, P. D., and Colburn, J. C., eds., *Capillary Electrophoresis: Theory and Practice*, Academic Press, Inc., New York (1992).
Haugland, *Handbook of Fluorescent Probes and Research Chemicals*, Molecular Probes, Inc., Eugene, Oreg. (1992).
Hobbs, Jr., et al., U.S. Pat. No. 5,151,507.
Hunziker, J., et al., "Nucleic Acid Analogues: Synthesis and Properties" in *Modern Synth. Methods* 7:331–417 (1995, ISSN 0176-7615).
Ji et al., *Anal. Chem.* 65:1323–1328 (1993).
Johnston, R. F., et al., *Electrophoresis* 11:355 (1990).
Keller and Manak, *DNA Probes, 2nd Ed.*, Stockton Press, New York (1993).
Khrapko, K. R., et al., *DNA Sequencing* 1:375 (1991).
Knudsen, H., et al., *Nucleic Acids Res.* 24:494–500 (1996).
Kricka, L. J., ed., *Nonisotopic DNA Probe Techniques*, Academic Press, Inc., New York (1992).
Kornberg and Baker, *DNA Replication, 2nd Ed.*, W. H. Freeman, San Francisco, Calif. (1992).
Mathies, R. A., et al., U.S. Pat. No. 5,091,652 (1992).
Matthews et al, *Anal. Biochem.* 169:1–25 (1988).
Menchen et al., PCT Publication No. WO 94/05688 (1994).
Menchen et al., U.S. Pat. No. 5,188,934.
Miller et al., *Nucleic Acids Res.* 16(3):9–10 (1988).
Montpetit et al., *J. Virol. Methods* 36:119–128 (1992).
Mullis et al., eds, *The Polymerase Chain Reaction*, BirkHauser, Boston, Mass. (1994).
Osborne, *CABIOS* 8:83 (1991).
Pirrung et al., U.S. Pat. No. 5,143,854.
Ploem, J. S., in *Fluorescent and Luminescent Probes for Biological Activity*, Mason, T. W., Ed., Academic Press, London, pp. 1–11 (1993).
Pon et al., *Biotechniques* 6:768–775 (1988).
Rosenblum et al., *Nucl. Acids Res.* 25:4500–4504 (1997).
Rychlik et al., *Nucleic Acids Res.* 17:8543–8551 (1989) and 18:6409–6412 (1990).
Sambrook et al., *Molecular Cloning: A Laboratory Manual, 2nd Edition*, Cold Spring Harbor Laboratory, New York (1989).
Scheit, *Nucleotide Analogs*, John Wiley Pub., New York (1980).
Schena, M., et al., *Science* 270:467 (1995).
Shalon, D., Ph.D. Dissertation, Falconer Library, Stanford University, California (1995).
Shoemaker et al., European Pub. No.EP 799,897 A1 (1997).
Taylor, J. S., *Nucl. Acids Res.* 13:8749 (1985).
Uhlman and Peyman, *Chem. Rev.* 90:543–584 (1990).
Walsh et al., *Biotechniques* 10(4): 506–513 (1991).
Wetmur, *Crit. Rev. Biochem. Mol. Biol.* 26:227–259 (1991).
Yershov, G., et al., *Proc. Natl. Acad. Sci.* 93:4913 (1996).

INTRODUCTION

Methods for detection and analysis of target nucleic acids have found wide utility in basic research, clinical diagnostics, forensics, and other areas. One important use is in the area of genetic polymorphism. Genetic polymorphisms generally concern the genetic sequence variations that exist among homologous loci from different members of a species. Genetic polymorphisms can arise through the mutation of genetic loci by a variety of processes, such as errors in DNA replication or repair, genetic recombination, spontaneous mutations, transpositions, etc. Such mutations can result in single or multiple base substitutions, deletions, or insertions, as well as transpositions, duplications, etc.

Single base substitutions (transitions and transversions) within gene sequences can cause missense mutations and nonsense mutations. In missense mutations, an amino acid residue is replaced by a different amino acid residue, whereas in nonsense mutations, stop codons are created that lead to truncated polypeptide products. Mutations that occur within signal sequences, e.g., for directing exon/intron splicing of mRNAs, can produce defective splice variants with dramatically altered protein sequences. Deletions, insertions, and other mutations can also cause frameshifts in which contiguous residues encoded downstream of the mutation are replaced with entirely different amino acid residues. Mutations outside of exons can interfere with gene expression and other processes.

Genetic mutations underlie many disease states and disorders. Some diseases have been traced directly to single point mutations in genomic sequences (e.g., the A to T mutation associated with sickle cell anemia), while others have been correlated with large numbers of different possible polymorphisms located in the same or different genetic loci (e.g., cystic fibrosis). Mutations within the same genetic locus can produce different diseases (e.g., hemoglobinopathies). In other cases, the presence of a mutation may indicate susceptibility to particular condition for a disease but is insufficient to reliably predict the occurrence of the disease with certainty. Most known mutations have been localized to gene-coding sequences, splice signals, and regulatory sequences. However, it is expected that mutations in other types of sequences can also lead to deleterious, or sometimes beneficial, effects.

The large number of potential genetic polymorphisms poses a significant challenge to the development of methods for identifying and characterizing nucleic acid samples and for diagnosing and predicting disease. In other applications, it is desirable to detect the presence of pathogens or exogenous nucleic acids and to detect or quantify RNA transcipt levels.

In light of the increasing amount of sequence data that is becoming available for various organisms, and particularly for higher organisms such as humans, there is a need for rapid and convenient methods for determining the presence or absence of target mutations. Ideally, such a method should have high sensitivity, accuracy, and reproducibility. Also, the method should allow simultaneous detection of multiple target sequences in a single reaction mixture.

SUMMARY OF THE INVENTION

In one aspect, the invention includes a method for detecting a target polynucleotide sequence. In the method, a target polynucleotide strand region and a target-complementary strand region are reacted with a first probe pair and a second probe pair under conditions effective for the first probe pair to hybridize to the first and second regions in the target strand region, forming a first hybridization complex, and for the second probe pair to hybridize to the first and second regions in the target-complementary strand region, forming a second hybridization complex. In one embodiment, the first probe pair comprises (i) a first polynucleotide probe containing a sequence that is complementary to a first target region in the target strand region and (ii) a second polynucleotide probe comprising a sequence that is complementary to a second target region in the target strand region, wherein the second region is located 5' to the first region and overlaps the first region by at least one nucleotide base, and the second probe pair may comprise (i) a third polynucleotide probe containing a sequence that is complementary to a first region in the target-complementary strand region and (ii) a fourth polynucleotide probe containing a sequence that is complementary to a second region in the target-complementary strand region, wherein the second region is located 5' to the first region and overlaps the first region by at least one nucleotide base.

Following hybridization, the second probe in the first hybridization complex and the fourth probe in the second hybridization complex can be cleaved to form (i) a third hybridization complex comprising the target strand region, the first probe, and a first fragment of the second probe having a 5' terminal nucleotide located immediately contiguous to a 3' terminal nucleotide of the first probe, and (ii) a fourth hybridization complex comprising the target-complementary strand region, the third probe, and a first fragment of the fourth probe having a 5' terminal nucleotide located immediately contiguous to a 3' terminal nucleotide of the third probe. The first probe may then be ligated to the hybridized fragment of the second probe to form a first ligated strand hybridized to the target strand region, and the third probe can be ligated to the fragment of the fourth probe to form a second ligated strand hybridized to the target-complementary strand region.

Denaturation of the first ligated strand from the target strand region, and of the second ligated strand from the target-complementary strand region, provides single stranded templates that can be hybridized to unreacted first and second probe pairs for additional probe cleavage and ligation, thereby increasing the amount of ligated probes. The occurrence of template-dependent ligation is evidence that the target sequence (or its complement) is present in a sample.

In one embodiment, the first region in the target strand region overlaps the second region in the target strand region by a single nucleotide base, and/or the first region in the target-complementary strand region overlaps the second region in the target-complementary strand region by a single nucleotide base. In another embodiment, the first region in the target strand region overlaps the second region in the target strand region by two nucleotide bases, and/or the first region in the target-complementary strand region overlaps the second region in the target-complementary strand region by two nucleotide bases.

In another embodiment, the 5' ends of the first and third probes terminate with a group other than a nucleotide 5' phosphate group, such as a nucleotide 5' hydroxyl group. In another embodiment, the 5' ends of the second and fourth probes terminate with a group other than a nucleotide 5' phosphate group. In another embodiment, the 5' ends of the first, second, third and fourth probes terminate with a group other than a nucleotide 5' phosphate group.

In another embodiment, the 3' ends of the second and fourth probes terminate with a group other than a nucleotide 3' hydroxyl group, such as a nucleotide 3' phosphate group. In another embodiment, the 3' ends of the second and fourth probes terminate with a group other than a nucleotide 3' phosphate group. In another embodiment, the 3' ends of the first, second, third and fourth probes terminate with a group other than a nucleotide 3' phosphate group.

In one embodiment, the first, second, third and fourth probes are provided as covalently separate entities. In another embodiment, the first probe pair comprises a first probe and a second probe in covalently linked form, such that the first probe is covalently linked by its 5' end to the 3' end of the second probe by a linking moiety. Similarly, the second probe pair may comprise a third probe and a fourth probe in covalently linked form, such that the third probe is covalently linked by its 5' end to the 3' end of the fourth probe by a linking moiety.

In another embodiment, at least one of the probes contains a detectable label. For example, at least one of the first probe or the third probe may contain a detectable label. Similarly, at least one of the second probe and the fourth probe may contain a detectable label. Preferably, the label is a non-radioactive label, and more preferably is a fluorescent label, although any suitable label can be used.

In practicing the present invention, any method may be employed to detect or measure probe ligation. In one embodiment, probe cleavage produces a second fragment from the second probe which does not associate with the third hybridization complex. Detection or measurement of the second fragment, directly or indirectly, is an indication that the target sequence is present. An increased amount of the second fragment in a reaction mixture can also be used to measure the extent of probe ligation in prior cycles of cleavage and ligation. Similarly, cleavage of the fourth probe can produce a fourth fragment which does not associate with the fourth hybridization complex. Detection or measurement of the fourth fragment, or of both the second and fourth fragments, directly or indirectly, can indicate that the target sequence is present.

In one embodiment, at least one of the second probe and the fourth probe contains both (i) a fluorescent dye and (ii) a quencher dye which is capable of quenching fluorescence emission from the fluorescent dye when the fluorescent dye is subjected to fluorescence excitation energy, and said cleaving severs a covalent linkage between the fluorescent dye and the quencher dye in the second probe and/or fourth probe, thereby increasing an observable fluorescence signal from the fluorescent dye.

In one embodiment, the second fragment is immobilized on a solid support for detection. In other embodiments, the second fragment is detected using electrophoresis or mass spectrometry.

The second fragment may be detected at any suitable time, such as continuously, or after a selected period of time, or after a selected number of cycles. another embodiment, the first ligated strand, the second ligated strand, or both, are measured after at least one cycle. For example, ligated strands can be immobilized on a solid support for detection, or can be detected using electrophoresis or mass spectrometry. In one embodiment, each detected ligated strand contains a fluorescent label.

In yet another embodiment, the reacting step further comprises providing a fifth polynucleotide probe which is complementary to a sequence variant of a sequence region to which either the first probe, second probe, third probe, or fourth probe is complementary. For example, the fifth polynucleotide probe and the first polynucleotide probe can be complementary to alternative polymorphic sequences. In one preferred embodiment, the fifth polynucleotide probe and the first polynucleotide probe contain different 3' terminal nucleotides that are complementary to alternative target nucleotide bases. Furthermore, the first and fifth polynucleotide probes may contain first and second detectable labels that are distinguishable from each other. Alternatively, the fifth and second polynucleotide probes can be complementary to alternative polymorphic sequences.

The first and second probe sets can be designed so that cleavage produces cleaved probes having flush abutting ends or staggered abutting ends. For example, to produce flush abutting ends, the first and third probes may be designed so that the 5' terminal base of the first region of the target strand region abuts the 5' terminal base of said first region of the target-complementary strand region. Alternatively, staggered ends can be produced when the 5' terminal base of the first region of the target strand region is separated by one or more bases from the 5' terminal base of the first region of the target-complementary strand region.

In yet another embodiment, the first and second probe pairs taken together constitute a first probe set, and the method further comprises reacting a sample with a plurality of different probe sets which are each designed to detect a different target polynucleotide sequence which may be present in the sample. In one embodiment, the method includes detecting at least one ligated strand produced by each different probe set when the corresponding target sequence is present. In one embodiment, ligated strands from different probe sets are detected by mass spectrometry. In another embodiment, ligated strands from different probe sets are detected by electrophoresis, based on distinct labels or electrophoretic mobilities, for example.

The first, second, third, or fourth probe in each probe set can be immobilized on distinct solid support regions. For example, prior to the reacting step, a probe from each set is immobilized on a distinct solid support region. In one embodiment, a probe in each probe set contains a distinct polynucleotide tag that identifies that probe set. These tags can be used to immobilize the probes to distinct solid support regions before, during, or preferably after cycles of cleavage and ligation, to facilitate detection of different target sequences. Such tags can be attached via any suitable position in the probes, such as the 5' end of the first probe in each different probe set, or the 3' end of the second probe in each different probe set, for example.

In another embodiment, for each probe set, the cleaving step releases a second fragment from the second probe of each probe set, and the method further includes detecting a second fragment for each target that is present. In one embodiment, the second fragments from different probe sets are detected by mass spectrometry. In another embodiment, second fragments are detected by electrophoresis, based on distinct labels, distinct electrophoretic mobilities, or both.

In another embodiment, a second fragment from each probe set contains a distinct polynucleotide tag that identifies that probe set. The tags can be used to immobilize the probes to distinct solid support regions, as above.

In another aspect, the methods described herein are modified so that the second probe pair is omitted, and one or more cycles of probe hybridization, cleavage, and ligation produce ligated strands at a rate that is linearly proportional to the number of cycles.

For example, the invention also includes a method for detecting a target polynucleotide sequence, comprising (a) reacting a target polynucleotide strand region with a first probe pair of the type described above, under conditions effective for the first and second probes in the probe pair to hybridize to the first and second regions in the target strand region, respectively, forming a first hybridization complex, (b) cleaving the second probe in the first hybridization complex to form (i) a second hybridization complex comprising the target strand region, the first probe, and a first fragment of the second probe having a 5' terminal nucleotide located immediately contiguous to a 3' terminal nucleotide of the first probe, (c) ligating the first probe to the hybridized fragment of the second probe to form a first ligated strand hybridized to the target strand region, (d) denaturing the first ligated strand from the target strand region, and (e) performing one or more additional cycles of steps (a) through (d), with the proviso that in the last cycle, step (d) is optionally omitted.

Kits and various assay components and reagents are also contemplated as discussed further herein. These and other features and advantages of the invention will become more readily apparent in light of the detailed description herein.

DETAILED DESCRIPTION

The present invention provides methods for detecting or quantifying one or more selected target polynucleotide sequences in a sample. The invention is highly accurate, permitting detection of target sequences with high specificity, and highly sensitive, allowing detection and/or quantitation of small amounts of target sequences. The invention is also advantageous for genotyping and detection of genetic polymorphisms.

Definitions

The following terms or phrases are intended to have the meanings below unless indicated otherwise.

"Nucleoside" refers to a compound containing a base-pairing moiety (also referred to as a "base") such as a purine, deazapurine, or pyrimidine nucleoside base, e.g., adenine, guanine, cytosine, uracil, thymine, deazaadenine, deazaguanosine, inosine, or any functional equivalent thereof, which is attached to a backbone moiety such as a sugar ring or any functional equivalent thereof. Nucleosides include naturally occurring nucleosides which contain a base-pairing moiety (A, C, G, T or U) linked to the 1-carbon of a pentose ring, 2'-deoxy and 2'-hydroxyl forms thereof (e.g., see Kornberg, 1992), and also pentose analogs and ring-open equivalents thereof (e.g., see Scheit, 1980; Uhlmann et al., 1990).

The term "nucleotide" as used herein refers to a phosphate ester of a nucleoside, e.g., a triphosphate ester, wherein the most common site of esterification is the pentose 5'-hydroxyl group. In certain cases, term "nucleoside" refers both nucleosides and nucleotides, for convenience. The terms nucleotide and nucleoside as used herein are intended to include synthetic analogs having modified nucleoside base moieties, modified sugar moieties, and/or modified phosphate groups and phosphate ester moieties, e.g., as described elsewhere (Scheit 1980; Eckstein, 1991).

"Polynucleotide" and "oligonucleotide" are interchangeable for purposes of this text and refer to a polymer of nucleoside monomers, including single, double and triple stranded deoxyribonucleotides, ribonucleotides, α-anomeric forms thereof, and the like. Usually the nucleoside monomers are linked by phosphodiester linkages, such that "phosphodiester linkage" refers to a phosphate ester bond or analog thereof wherein the phosphorous atom is in the +5 formal oxidation state and one or more of the oxygen atoms is replaced with a non-oxygen moiety. Exemplary phosphate analogs include phosphorothioate, phosphorodithioate, phosphoroselenoate, phosphorodiselenoate, phosphoroanilothioate, phosphoranilidate, phosphoramidate, boronophosphates, and the like, including associated counterions, e.g., $H^+$, $NH_4^+$, $Na^+$, and the like, if such counterions are present. "Polynucleotides" and "oligonucleotide" also include polymers of non-nucleotidic monomers, linked by phosphate ester or other linkages, which are capable of forming sequence-specific hybrids with a target nucleic acid, e.g., peptide nucleic acids (PNAs, e.g., see Knudsen, 1996). Chimeric structures containing more than one type of linkage and/or nucleotide subunit are also contemplated. Polynucleotides typically range in size from a few monomeric units, e.g. 8–40, to hundreds or thousands of monomeric units. Whenever a polynucleotide is represented by a sequence of letters, such as "ATGCCTG," it will be understood that the nucleotides are in 5' to 3' order from left to right and that "A" denotes deoxyadenosine, "C" denotes deoxycytidine, "G" denotes deoxyguanosine, and "T" denotes thymidine, unless otherwise noted.

"Polynucleotide probe" refers to any moiety that can hybridize, via hydrogen binding, to a target nucleic acid sequence with sequence specificity that is suitable for the purposes of the present invention.

"Target-specific polynucleotide" refers to a polynucleotide having a target-binding segment that is perfectly or substantially complementary to a target sequence, such that the polynucleotide binds specifically to an intended target without significant binding to non-target sequences under sufficiently stringent hybridization conditions.

"Label" means any moiety that, when attached to a nucleotide or polynucleotide, renders such nucleotide or polynucleotide detectable using known detection methods.

"Diagnosis" is intended to encompass diagnostic, prognostic, and screening methods.

"Ligation-incompetent" refers to an entity that, under particular conditions, is incapable of undergoing template-dependent ligation by a ligation enzyme.

"Ligation-blocked" refers to an entity that is chemically incapable of undergoing ligation under any conditions until a blocking group is removed.

Samples

The target nucleic acids for use with the invention may be derived from any organism or other source, including but not limited to prokaryotes, eukaryotes, plants, animals, and viruses, as well as synthetic nucleic acids, for example. The target nucleic acids may originate from any of a wide variety of sample types, such as cell nuclei (e.g., genomic DNA), whole cells, tissue samples, phage, plasmids, mitrochondria, and the like. The target nucleic acids may contain DNA, RNA, and/or variants or modifications thereof.

Many methods are available for the isolation and purification of target nucleic acids for use in the present invention. Preferably, the target nucleic acids are sufficiently free of proteins and any other interfering substances to allow adequate target-specific probe annealing, cleavage, and ligation. Exemplary purification methods include (i) organic extraction followed by ethanol precipitation, e.g., using a phenol/chloroform organic reagent (Ausubel), preferably with an automated DNA extractor, e.g., a Model 341 DNA Extractor available from PE Applied Biosystems (Foster City, Calif.); (ii) solid phase adsorption methods (Walsh, 1991; Boom); and (iii) salt-induced DNA precipitation methods (Miller), such methods being typically referred to as "salting-out" methods. Optimally, each of the above purification methods is preceded by an enzyme digestion step to help eliminate protein from the sample, e.g., digestion with proteinase K, or other proteases.

To facilitate detection, the target nucleic acid can be amplified using a suitable amplification procedure prior to conducting the hybridization, cleavage, and ligation steps of the present invention. Such amplification may be linear or exponential. In a preferred embodiment, amplification of the target nucleic acid is accomplished using the polymerase chain reaction (PCR) (e.g., Mullis et al., 1994). Generally, the PCR consists of an initial denaturation step which separates the strands of a double stranded nucleic acid sample, followed by repetition of (i) an annealing step, which allows amplification primers to anneal specifically to positions flanking a target sequence; (ii) an extension step which extends the primers in a 5' to 3' direction thereby forming an amplicon nucleic acid complementary to the target sequence, and (iii) a denaturation step which causes the separation of the amplicon from the target sequence. Each of the above steps may be conducted at a different temperature, preferably using an automated thermocycler (PE Applied Biosystems, Foster City, Calif.). If desired, RNA samples can be converted to DNA/RNA heteroduplexes or to duplex cDNA by known methods (e.g., Ausubel; Sambrook).

Method

The present invention employs probe pairs that are each designed to hybridize to a complementary target sequence, and which are capable of undergoing specific cleavage and ligation when hybridized to the target sequence. The probe pairs are useful, for example, in linear and exponential probe ligation methods described herein. Any of a variety of different probe constructs and configurations can be used, as will be more fully understood from the following discussion.

Typically, each probe pair comprises (i) a first polynucleotide probe containing a sequence that is complementary to a first target region in the target strand region and (ii) a second polynucleotide probe comprising a sequence that is complementary to a second target region in the target strand region. The second region is located 5' to the first region and overlaps the first region by at least one nucleotide base. Probes can be prepared by any suitable method, preferably using an automated DNA synthesizer and standard chemistries, e.g., phosphoramidite chemistry (Beaucage; Gait, 1984, 1990).

In one aspect, the invention includes a method for detecting a target polynucleotide sequence. In the method, a target polynucleotide strand region is reacted with a first probe pair under conditions effective for first and second probes of the probe pair to hybridize to the first and second regions in the target strand region, respectively, forming a first hybridization complex. Following hybridization, the second probe in the first hybridization complex can be cleaved to form a hybridization complex comprising the target strand region, the first probe, and a first fragment of the second probe having a 5' terminal nucleotide located immediately contiguous to a 3' terminal nucleotide of the first probe. The first probe may then be ligated to the hybridized fragment of the second probe to form a first ligated strand hybridized to the target strand region. After separation of the first ligated strand from the target strand region by denaturation, the target strand region in single-stranded form can be hybridized to a new probe pair for additional probe cleavage and ligation, thereby increasing the amount of ligated probe. The occurrence of template-dependent ligation is evidence that the target sequence is present in a sample.

In one embodiment, the first region overlaps the second region by a single nucleotide base. In another embodiment, the first region overlaps the second region by two nucleotide bases. The invention also contemplates embodiments in which the first and second regions overlap by 3, 4, 5, 6, 7, 8, 9, 10 or more nucleotides.

An exemplary embodiment is illustrated in Scheme I below, which shows a single-stranded target strand region (T0) aligned with first polynucleotide probe (P1) and second polynucleotide probe (P2) of a first probe pair. The two probes are shown in a 5' to 3' orientation (left to right), whereas the target is shown in a 3' to 5' orientation. The target strand region, which is the complement of the human ApoB sequence shown in Example 1, contains a first region (R1) and an adjacent region (R2) that is located 5' to the first region. "X" indicates bases that flank the two target regions and which are not hybridized to the first and second probes.

(2) is a substrate for certain 5' nuclease enzymes (referred to herein as 5' nucleases or 5' nuclease enzymes) which recognize hybrid structures containing first and second polynucleotide moieties that have overlapping target-complementary ends when hybridized to a complementary strand. In the presence of such a 5' nuclease, the second probe in the complex can be cleaved to form a cleaved hybridization complex comprising the target strand, the first probe, and a first fragment of the second probe having a 5'

Scheme Ia

```
P2                              5'-ACTGCGAGGTCACTGTGAGTTTTC-3'     (SEQ ID NO:5)
P1: 5'-AAGAAATTATCTCGGTCCTCACAATAAA-3' (SEQ ID NO:16)
                                |<----------R2---------->|
       |<------------R1------------>|
T0: 3'-XXTTCTTTAATAGAGCCAGGAGTGTTATTTGACGCTCCAGTGACACTCAAAAGXX-5'(SEQ ID NO:17)
```

In Scheme Ia, the first region and second region overlap by a single base. The first probe consists of 28 contiguous bases that are complementary to the corresponding bases in region R1. The first probe preferably contains a 3'-hydroxyl group (–OH). The second probe consists of 24 contiguous bases that are complementary to corresponding bases in region R2. When both the first probe and the second probe are hybridized to the target strand region, the 3' terminal A base of the first probe is aligned with the 5' terminal A base of second probe, such that both A bases may compete for hybridization to the corresponding T base in the target strand region (in bold type and underlined). In other words, the target-complementary segments of the first and second probes (which hybridize to R1 and R2) overlap by one base when they are hybridized fully to the target sequence.

Hybridization of the first and second probes to the target sequence produces a ternary complex can be referred to as a "displaced strand structure", wherein the overlapping ends of the hybridized first and second probes can compete for hybridizing to the same complementary bases in the target strand region. It is possible that the overlapping ends may exist in an equilibrium between states wherein (i) the 3' end of the first probe is hybridized directly to the target strand region, displacing the 5' end of the second probe, (ii) the 5' end of the second probe is hybridized directly to the target strand region, displacing the 3' end of the first probe, (iii) the overlapping ends form a triplex structure involving Hoogsteen or reverse Hoogsteen basepairing, or (iv) any other possible equilibrium state(s). This hybridization complex (1) is ligation-incompetent, meaning that the abutting ends are not readily ligatable in the presence of a template-dependent ligase enzyme, due to the absence of abutting, adjacent termini that are matched to complementary target bases, and terminal nucleotide located immediately contiguous to a 3' terminal nucleotide of the first probe.

With reference to the complex formed upon hybridization of the first and second probes with the target strand from Scheme I, cleavage causes severance of the 5' terminal base from the second probe, leaving the first probe and a fragment of the second probe hybridized to the target strand. The resultant complex is illustrated in Scheme Ib, in which the first probe and the remaining fragment of the second probe are shown on different lines to emphasize that their abutting ends are immediately contiguous with each other but are not covalently linked. The 5'-end of the remaining fragment from the second probe contains a 5'-phosphate group due to the action of the 5' nuclease.

Scheme Ib

```
P2                                  5'-CTGCGAGGTCACTGTGAGTTTTC-3'   (SEQ ID NO:18)
P1:   5'-AAGAAATTATCTCGGTCCTCACAATAAA-3' (SEQ ID NO:16)
T0: 3'-XXTTCTTTAATAGAGCCAGGAGTGTTATTTGACGCTCCAGTGACACTCAAAAGXX-5'(SEQ ID NO:17)
```

The hybridization complex in Scheme Ib is ligation-competent since the abutting ends of the first probe and the fragment of the second probe have chemical groups (a 3' hydroxyl and a 5' phosphate) which are amenable to ligation under appropriate conditions. For example, treatment of the cleaved complex with a ligase enzyme is effective to produce a ligated strand (LS1) hybridized to the target strand, as illustrated in Scheme Ic.

Scheme Ic

```
LS1:  5'-AAGAAATTATCTCGGTCCTCACAATAAACTGCGAGGTCACTGTGAGTTTTC-3'   (SEQ ID NO:19)
T0: 3'-XXTTCTTTAATAGAGCCAGGAGTGTTATTTGACGCTCCAGTGACACTCAAAAGXX-5'(SEQ ID NO:17)
```

Following denaturation of the ligated strand from the target strand, the target strand can be hybridized to a new probe pair, and probe cleavage and ligation can be repeated to form another ligated strand. Formation of such ligated strands indicates that the target sequence is present in the sample.

Schemes Ia to Ic illustrate a process that can be carried out to convert multiple copies of a probe pair (which is present in excess relative to the amount of the target strand) into ligated strands at a linear rate that depends on the duration of each cycle of hybridization, cleavage, ligation, and denaturation.

In a further embodiment, exponential production of ligated strands can be achieved using first and second probe pairs which are targeted to a target strand region and a complement of the target strand region, respectively. An example of such an embodiment is illustrated below with reference to Schemes IIa–IId.

Scheme IIa shows a partial duplex sequence for an "A allele" of the gene for human ligase I ("AHL", for A allele of human ligase I), aligned with complementary first and second probe pairs. The probes (Ap1 and Ap2) of the first probe pair are complementary to first and second regions (R1 and R2) of the target strand region T1. The first and second probes (Ap3 and Ap4) of the second probe pair are complementary to first and second regions (R3 and R4) in the complementary target strand region T2.

It will be appreciated that in many situations, designation of the two strands of a duplex target as a "target strand" and "complement of the target strand" will be an arbitrary choice, so that reversal of these designations may also be appropriate. For example, a gene-coding strand can be designated as a "target strand" or as a "complement of a target strand", depending on the preference of the user. Alternatively, both strands of a target duplex can be referred to as "target strands".

Also, when multiple probe pairs are used to detect a multiple possible target sequences in a sample, it will be appreciated that the different target sequences may be present in the same target strand (i.e., in the sample chromosome or same restriction fragment) or may be present in different strands. For this reason, the phrase "target poly-

Scheme IIa

```
Ap1:    5'-AaCCTCACAGAGGCTGAAGTGGCA-3' (SEQ ID NO:8)
Ap2:                           5'-aAACAGAGAAGGAAGGAGAAGACGG-3' (SEQ ID NO:9)
          |<---------R1--------->|
                             |<----------R2---------->|
T1      3'-TTTCGGAGTGTCTCCGACTTCACCGTTGTCTCTTCCTTCCTCTTCTGCCCC-5' (SEQ ID NO:20)
T2:     5'-AAAGCCTCACAGAGGCTGAAGTGGCAACAGAGAAGGAAGGAGAAGACGGGG-3' (SEQ ID NO:2)
          |<---------R4--------->|
                             |<----------R3---------->|
Ap3:                            3'-TTGTCTCTTCCTTCCTCTTCTGCCaa-5' (SEQ ID NO:10)
Ap4:       3'-GGAGTGTCTCCGACTTCACCGTa-5' (SEQ ID NO:11)
```

The first probe (Ap1) of the first probe pair contains 24 nucleotides. The 5' terminal base of Ap1 is matched with respect to a corresponding T base in the target. The second base from the 5' end of Ap1 is mismatched with respect to a C base in T1. Bases 3 to 24 in Ap1 constitute a sequence of 22 contiguous target-complementary bases with respect to strand region T1. The second probe (Ap2) contains 25 nucleotides, of which the 5'-terminal A base is mismatched with respect to a corresponding G base in strand region T1, and the remaining bases constitute a sequence of 24 contiguous matching bases with respect to T1. Thus, the target regions (R1 and R2) to which the first probe pair binds are 22 and 24 nucleotides in length, respectively, and overlap by a single base.

With reference to the second probe pair, the first probe (Ap3) contains 26 nucleotides, of which the first two bases at the 5' end are mismatched with respect to two G bases in target strand region T2 (the human ligase I encoding strand region, which is complementary to target strand region T1), and the remaining bases are complementary to corresponding bases in T2. The second probe (Ap4) contains 23 nucleotides, of which the 5'-terminal base is mismatched with respect to a corresponding A base in T2, and the remaining bases are complementary to corresponding bases in T2. Thus, the target regions (R3 and R4) the first and second regions in strand region T2 are 24 and 22 nucleotides in length, respectively, and the two regions overlap by a single base.

nucleotide strand region" or "target strand region" is used to refer to a target sequence regardless of whether two different target sequences are present in the same strand.

When both probes of the first probe pair are hybridized to strand region T1, the 3' terminal A base of the first probe is aligned with an overlapping A base at the 5' end of the target-complementary region of the second probe, such that these two overlapping bases may compete for hybridization to the corresponding target T base (in bold type with underlining) in strand region T1. Similarly, when both probes of the second probe pair are hybridized to strand region T2, the 3' terminal T base of the first probe is aligned with an overlapping T base at the 5' end of the target-complementary region of the second probe, such that these two overlapping bases may compete for hybridization to the corresponding target A base (in bold type with underlining) in strand region T2.

Hybridization of each probe pair to a complementary sequence in T1 or T2 produces a hybridization complex that is (1) ligation-incompetent, and (2) a substrate for certain 5' nucleases as discussed herein. Prior to hybridization, a duplex target should be denatured to separate the complementary strands of the target, followed by annealing of the separated strands with their complementary probe pairs. The presence of an excess of each probe pair favors formation of probe-target complexes and helps minimize reformation of the target duplex. Resultant complexes are illustrated in Scheme IIb.

Scheme IIb

```
Ap1:    5'-AaCCTCACAGAGGCTGAAGTGGCA-3' (SEQ ID NO:8)
Ap2:                              5'-ACAGAGAAGGAAGGAGAAGACGG-3'    (SEQ ID NO:21)
T1:   3'-TTTCGGAGTGTCTCCGACTTCACCGTTGTCTCTTCCTTCCTCTTCTGCCCC-5'(SEQ ID NO:20)
                                 and
Ap3:                                3'-TTGTCTCTTCCTTCCTCTTCTGCCaa-5' (SEQ ID NO:10)
Ap4:   3'-GGAGTGTCTCCGACTTCACCG-5' (SEQ ID NO:22)
T2:  5'-AAAGCCTCACAGAGGCTGAAGTGGCAACAGAGAAGGAAGGAGAAGACGGGG-3'(SEQ ID NO:2)
```

In each complex, the first probe and the remaining fragment of the second probe have abutting ends that are immediately contiguous with each other but are not yet covalently linked. The 5'-end of the remaining fragment from the second probe contains a 5'-phosphate group due to the action of the 5' nuclease enzyme. Each hybridization complex in Scheme IIb is ligation-competent since the abutting ends of the first probe and the fragment of the second probe have chemical groups (a 3' hydroxyl and a 5' phosphate) which are amenable to ligation under appropriate conditions. Ligation of the abutting ends in each complex produces a ligated strand (LS 11 or LS 12) hybridized to the target strand region, as illustrated in Scheme IIc.

hybridization, cleavage, and ligation is effective to produce a ligated strand that contains a contiguous sequence complementary to the target sequence (target strand region) in the initial target strand. This ligated, complementary strand can then serve as a template for binding of a second probe pair to form a ligated strand that contains a sequence identical to a corresponding sequence in the initial target strand.

As noted above, the first and second probes in each probe pair contain sequences that are complementary to first and second target regions in the target strand, respectively, such that the target regions overlap each other by at least one nucleotide base. The target regions are preferably selected to be within an invariant target sequence that will be present in Scheme IIc

```
LS11:    5'-AaCCTCACAGAGGCTGAAGTGGCAACAGAGAAGGAAGGAGAAGACGG-3'(SEQ ID NO:23)
T1:    3'-TTTCGGAGTGTCTCCGACTTCACCGTTGTCTCTTCCTTCCTCTTCTGCCCC-5'(SEQ ID NO:20)
                                 and
LS12:      3'-GGAGTGTCTCCGACTTCACCGTTGTCTCTTCCTTCCTCTTCTGCCaa-5' (SEQ ID NO:24)
T2:   5'-AAAGCCTCACAGAGGCTGAAGTGGCAACAGAGAAGGAAGGAGAAGACGGGG-3'(SEQ ID NO:2)
```

Following separation of the ligated strand from the target strand region, the ligated strand and target strand region can each be hybridized to another first or second probe pair, and the steps of probe cleavage and ligation can be repeated to form another ligated strand. After each cycle of hybridization, cleavage, ligation, and strand separation, the sum of ligated probes is expected to be equal to $C \times 2^N$, where C is the initial amount of the target sequence in the sample, and N is the number of cycles, assuming 100% yield at each step. The formation of ligated strands indicates that the target sequence is present in the sample.

As more cycles of hybridization, cleavage, ligation, and strand separation are performed, probe ligation products become the predominant template for probe hybridization, cleavage, and ligation, and the product mixture becomes dominated by duplexes formed from ligation of the first and second probe pairs to form complementary ligated strands as shown in Scheme IId. Double underlining indicates the A and T bases derived from the 3'-terminal bases of the first probes in the first and second probe pairs, respectively.

the sample if the target (e.g., a gene, a heterologous target nucleic acid, or a pathogen nucleic acid) is present in the sample. Thus, the target-complementary sequence in each probe is usually designed to be perfectly complementary to its respective target region. Furthermore, it is preferred that the portions of the probes that bind the first and second target regions in the vicinity of the cleavage/ligation site be perfectly complementary to the target strand region. In other words, hybridization may be successful if a target-complementary sequence is substantially complementary, provided that site-specific probe cleavage and subsequent ligation are not significantly impeded by mismatched bases. However, it may be desirable to design a first or second probe in a probe pair that includes a nucleotide base that is deliberately mismatched with respect to the target, but is located near (e.g., within 2 to 4 bases of) the locus of probe cleavage and ligation (or near a known polymorphic site), to destabilize probe hybridization with non-target sequences.

By way of illustration only, if the 3' base of the first probe is mismatched with respect to a corresponding base in the Scheme IId

```
LS11:5'-AaCCTCACAGAGGCTGAAGTGGCAACAGAGAAGGAAGGAGAAGACGG-3'   (SEQ ID NO:23)
LS12:   3'-GGAGTGTCTCCGACTTCACCGTTGTCTCTTCCTTCCTCTTCTGCCaa-5'(SEQ ID NO:24)
```

It will also be appreciated that if a sample initially contains only a single-stranded target (i.e., there is no complementary strand), or if the ratio of target to its complementary strand is less than 1:1, then the first cycle of probe target strand region, cleavage of a hybridized second probe is possible if the aligned base in the second probe is within a probe sequence that is complementary to the target. However, the presence of the 3' mismatch can thereafter inhibit or prevent ligation of the first probe to the remaining fragment of the second probe. If the second region of a target strand region contains a base mutation immediately 5' to the target base to which the 3'-end of the first probe is complementary, then the mismatch with the second probe can prevent stable formation of a hybridization complex that is necessary for site-specific cleavage of the second probe.

In some situations, a target sequence may be susceptible to rapid sequence mutation, as in the case of HIV and other pathogenic organisms. For such situations, the probes should be targeted to a conserved target region if possible, or at least to a target region that has a minimum number of potential base variations. Alternatively, when potential sequence variants are known, several different probes can be included in the reaction, each targeted to a different target sequence variant, to ensure that the target sequence is detected. Similar strategies can be used to detect allelic variants and single nucleotide polymorphisms (SNPs) as appropriate.

It should also be noted that when first and second probe pairs are used that are complementary to the two complementary strands of a target duplex (as in Schemes IIa to IId), the two probe pairs can be designed such that the cleavage sites in the second probes of each pair are directly aligned with each other, or are staggered relative to each other. For example, the 3' ends of the first probes in the first and second probe pairs in Scheme IIa (Ap 1 and Ap3) overlap each other by a single base. Overlaps of more than one base (e.g., 2, 3, 4, or more bases) are also contemplated. Similarly, probe pairs can also be designed such that the 3' ends of the second probes in each pair abut each other (zero overlap), or are recessed relative to each other to create gaps of one or more bases between their 3' ends (e.g., gaps of 1, 2, 3, 4, 5 or more bases). The choice of probe design to achieve a particular overlap or recess can be optimized for particular experimental conditions and sample to reduce no-template or non-specific ligations by adjusting temperature, cycle times, and other experimental parameters as desired.

The length of the target-complementary sequence in each probe is selected to ensure specific hybridization of the probe to the desired target region, preferably without significant cross-hybridization to non-target sequences in the sample. One advantage of using a target-specific probe pair to detect a target sequence is that both probes must bind to first and second regions of a target sequence. If only one of the first and second probes is hybridized to a complementary strand region, then cleavage and ligation to the other probe does not occur.

The target complementary sequences of the probes can be of any length suitable for practice of the invention. In general, the lengths of the target-complementary sequences in the probes should be sufficiently long to allow specific detection of the target sequence, without significant interference from hybridization to non-target sequences. Typically, the target-complementary sequence in a probe is at least 8, 10, 15, or 18 nucleotides in length. Preferred length ranges for the target-complementary sequences are 8 to 40 nucleotides, 10 to 35 nucleotides, 15 to 30 nucleotides, and 18 to 24 nucleotides. When two probe pairs are used to bind to the two strands of a target duplex, respectively, or when multiple probe pairs are used to detect different target sequences, the melting temperatures of the probes, when hybridized to their complementary target sequences, preferably fall within a ΔTm range (Tmax–Tmin) of 15° C. or less, 10° C. or less, and preferably 5° C. or less. Probe pairs that have similar melting temperatures are also advantageous to obtain better uniformity in hybridization kinetics, so that within-cycle yields are comparable for different probe pairs.

Melting temperatures of probes can be calculated using known methods for predicting oligonucleotide melting temperatures (Breslauer, 1986; Rychlik, 1989 and 1990; Wetmur, 1991; Osborne, 1991; Montpetit, 1992) for example. Target-complementary probe sequences between about 18 and 24 bases in length are preferred because such polynucleotides tend to be very sequence-specific when the annealing temperature is set within a few degrees of an oligonucleotide melting temperature (Dieffenbach, 1995). Probe characteristics can be further optimized by empirical methods, if desired.

When a hybridization complex has formed between a probe pair and a complementary target sequence, cleavage of the second probe in a target hybridization complex may be accomplished using any conditions and reagents that are effective to achieve the desired result. Preferably, cleavage is accomplished using an enzyme from the FEN (5' flap endonuclease) family of enzymes (also referred to as 5' nucleases, 5' endonucleases, and 5' exo/endonucleases), or a multi-enzyme polypeptide having FEN activity. For the following discussion, polypeptides that contain FEN activity are referred to collectively as 5' nucleases. Non-polymerase 5' nucleases can be obtained from *E. coli*, yeast, mouse, human, Pyrococcus furiosus, Pyrococcus woesei, Methanococcus jannaschii, and Archaeglobus fulgidus (e.g., see D. J. Hosfield et al., *J. Biol. Chem.* 273:27154 (1998); B. Shen et al., *Trends Biochem. Sci.* 23:171 (1998); PCT Pub. WO 98/42873; and U.S. Pat. No. 5,874,283 (Harrington et al.)). Numerous DNA polymerase enzymes have been shown to contain 5' nuclease activity, including DNA polymerases from Thermus aquaticus, Thermus flavus, Thermus thermophilus, and Bacillus stearothermophilus (e.g., see WO 97/27214, WO 98/23774, and WO 98/42873). In many cases, genes for these enzymes have been introduced into host organisms suitable for expressing large amounts of enzyme. Also useful are truncated or modified DNA polymerase polypeptides which can be generated by recombinant or proteolytic methods, and have (i) reduced polymerase activity (but retain nuclease activity) and/or (ii) enhanced 5' nuclease activity, chimeric and fusion polypeptides with 5' nuclease activity, and 5' nuclease mutants (e.g., see WO 98/42873). A variety of enzymes having 5' nuclease activity are available from Third Wave Technologies, Madison, Wis., as well as various academic laboratories.

The cleavage and ligation steps described herein can be performed under any appropriate conditions that provide desired results. Buffer conditions can be found in references such as described above with respect to nuclease cleavage, and in references described below with respect to ligation (see also Examples 1 and 2 below). Typical buffers include Tris, MOPS, Tricine, Bicine, MOBS, and other available buffers (e.g., see Sigma-Aldrich Catalog regarding "Good buffers"). Buffer concentrations of 5 to 100 mM are typically useful, although higher or lower concentrations can also be used. Salts and other additives, such as NaCl, LiCl, KCl, glycerol (e.g., 1–10 volume percent) and the like can also be included if desired, as well as appropriate cofactors for the particular enzymes that are used (e.g., $MgCl_2$ or $MnCl_2$ for some nucleases).

As noted above, cleavage occurs in the second probe at the internucleotide linkage located immediately 3' of the base that aligns with the 3' most base of the first probe, when the first and second probes are hybridized to the correct target sequence. The cleavage reaction produces a fragment of the second probe that remains hybridized to the target strand region, and also a second fragment of the second probe that diffuses from the target strand. If the first and second target regions in the target strand overlap by a single base, then the diffusive second fragment contains the target-complementary base from the second probe that was immediately 5' of the cleavage site, plus any other groups linked to that base. If the first and second target regions in the target strand overlap by four target-complementary bases, for example, then the diffusive second fragment contains, at its 3' end, the segment of four target-complementary bases from the second probe that were immediately 5' to the cleavage site, plus any other attached groups.

The cleavage reaction catalyzed by the 5' nuclease enzyme can be described as being both structure-specific and sequence-specific. The reaction is structure-specific because the 5' nuclease enzyme specifically cleaves an internucleotide linkage in the second probe between a first base that is aligned with the 3' terminal base of the first probe and a second base that is 3' to the first base, regardless of the particular sequences of the first probe, second probe, and target strand region. The reaction is sequence-specific because the site of cleavage, relative to the target sequence, is determined by the target-complementary sequences of the first and second probes, and also by the length of overlap between the target-complementary sequences of the probes.

Preferably, the 5' nuclease enzyme is a thermostable enzyme that retains substantially full activity after multiple cycles (e.g., 30 cycles) of heating and cooling, so that there is no need to replenish 5' nuclease enzyme during cycling. Such enzymes can be readily obtained from thermophilic organisms as indicated above. In an exemplary preferred embodiment, the enzyme retains at least 80% of initial 5' nuclease activity after thirty cycles of 65° C. for 1 min. (annealing/cleaving/ligation) and 95° C. for 15 seconds (strand denaturation).

According to one embodiment, the second probe in a probe pair contains one or more cleavage-resistant intemucleotide linkages to reduce or prevent cleavage of the probes at linkage sites other than the intended cleavage site. Such cleavage-resistant linkages may include phosphorothioates (5' S, 3' S, or exo S), phosphorodithioates (e.g., di-exo or di-endo), phosphoramidates (5' to 3' N, 3' to 5' N, or exo-N), O-methyl phosphonates, and peptide nucleic acid linkages, etc., for example. Methods for synthesizing such linkages are well known, and are described, for example, in U.S. Pat. No. 5,837,835 (Gryaznov et al.), U.S. Pat. No. 5,859,233 (Hirschbein et al.), Hunziker et al. (1995), and Uhlmann et al. (1990). In one embodiment, the intersubunit linkages of the target-complementary portion of the second probe are all cleavage-resistant linkages except for the linkage that is to be cleaved. However, the occurrence and extent of probe cleavage at secondary sites (other than the intended linkage) may be sequence-dependent or, for other reasons, may be limited to only a few linkages within a probe. These secondary sites can be identified and characterized by electrophoretic or other methods, upon which particularly susceptible linkages can be replaced with cleavage-resistant linkages, while stable linkages remain as standard phosphodiester linkages.

It will be appreciated that the effectiveness of a particular type of linkage may depend on the particular 5' nuclease that is used. For example, some endonucleases can more readily cleave exo-S phosphorothioate linkages having Rp chirality than linkages having Sp chirality (see Taylor et al., 1985). Also, the presence of one or more PNA linkages close to the target cleavage site may inhibit enzyme binding, so that such linkages may be most useful if located at least several (e.g., at least 5) linkages from the linkage that is to be cleaved. The use and placement of a particular linkage type within a probe is a matter of design choice of the user and the requirements of a particular assay.

After site-specific cleavage of the second probe, the first probe and remaining fragment of the second probe are ligated to form a ligated strand. The ligation step is accomplished using any suitable conditions that are effective to promote covalent ligation of abutting target-complementary termini of contiguously hybridized first probe and cleaved second probe. Usually, ligation can be accomplished enzymically using a ligase enzyme. In a preferred mode, ligation entails coupling the 3' terminal 3' hydroxyl group of the first probe to a 5' phosphate group of cleaved second probe, to produce a ligated strand that is connected by a standard phosphodiester linkage. However, any other combination of reactive groups can be used, as long as ligation occurs when the probes are bound to the intended target sequence.

Numerous ligase enzymes are known in the art and can be obtained from a variety of biological and commercial sources. Exemplary ligases include, but are not limited to, E. coli ligase, T4 ligase, T. aquaticus ligase, T. Thermophilus ligase, Pfu ligase, etc. (see, for example, U.S. Pat. No. 5,830,711 (Barany et al.) and EP Patent 320308 B1 (Backman and Wang). A thermostable ligase is preferred so that there is no need to replenish ligase activity during temperature cycling. In an exemplary preferred embodiment, the enzyme retains at least 80% of initial 5' nuclease activity after thirty cycles of 65° C. for 1 min. (annealing/extension) and 95° C. for 15 seconds (strand denaturation).

Although it is preferred that ligation is carried out using a ligase enyzme, chemical (non-enzymic) ligation is also contemplated. In one embodiment, chemical ligation can be performed by generating a chemically reactive group at the 5' end of the remaining fragment of the second probe that is capable of reacting with a corresponding reactive group at the 3' end of hybridized first probe. When the 3' base of the first probe is immediately contiguous with the 5' base of the fragment of the second probe, and the 3' base and 5' base are hybridized to matching bases in the target strand region, the two reactive groups form a covalent linkage due to mutual close proximity. The reaction occurs at the temperature of the reaction mixture and does not require illumination with high energy light, although microwave irradiation can be used to facilitate ligation. For example, the first probe can be designed to contain a 3' bromoacetyl amino group, and the second probe can be designed to contain a phosphorothioate linkage at the site that is to be cleaved. Cleavage of the second probe produces a 5' thiophosphate group that is immediately contiguous with the 3' bromoacetyl amino group. Displacement of the bromine by the sulfur atom of the thiophosphate group produces a thiophosphorylacylamino linkage between the first probe and the remaining second fragment of the second probe. The resultant ligated strand can then be detected or can serve as a template for hybridization, cleavage, and ligation of a complementary second probe pair. Guidance for exemplary chemical groups that may be used for thermal chemical ligation can be found, for example, in U.S. Pat. No. 5,476,930 (Letsinger and Gryaznov), U.S. Pat. No. 5,741,643 (Gryaznov et al.), and references cited therein. Chemical ligation by photoexcitation is also contemplated, as described in EP Patent 324616 B1 (Royer et al.), for example.

The probe pairs used in the present invention are designed to be ligation-incompetent when first and second probes are hybridized to their corresponding first and second target regions, due to the inability of the two probes to form a nicked duplex structure with suitably reactive abutting probe ends. A correctly hybridized probe pair becomes ligation competent only after site-specific cleavage of the second probe as discussed above. Generally, the "nicked duplex" that is produced after cleavage is readily ligated by ligase enzyme (enzymic embodiments) or chemical coupling (chemical embodiments) because the abutting ends of the first probe and cleaved second probe are close to each other due to hybridization to the target strand region. However, incorrect ligation reactions are also possible due to erroneous probe cleavage events, template-independent ligation reactions, and template-dependent reactions resulting from spurious duplex formation. Such side reactions can be inhibited by providing probes with ligation blocked ends. For example, since the 5' ends of the probes in the probe pairs do not participate in target-specific ligation, they can be rendered "ligation blocked" by providing 5' end groups that are incapable of ligation under the reaction conditions of the invention. Thus, in an enzymic ligation embodiment, the probes can be rendered ligation blocked by providing a 5' terminal group that is not a nucleotide 5' phosphate. Such non-ligatable blocking groups can be any of a large variety of chemical entities, such as 5' deoxy, 5'hydroxy, 5' N-acetyl, 5' O-trityl, 5' O-monomethoxytrityl, etc. For example, when first and second probe pairs are used that are complementary to both strands of a duplex target, the 5' ends of the first and third probes terminate with a group other than a nucleotide 5' phosphate group, and/or the 5' ends of the second and fourth probes terminate with a group other than a nucleotide 5' phosphate group, such as 5' hydroxyl.

Similarly, the 3' ends of the second probe in each probe pair can be rendered ligation-blocked by providing a 3' terminal group that is not a nucleotide 3' hydroxyl group. Exemplary 3' blocking groups include 3' deoxy, 3' phosphate, 3' N-acetyl, 3' O-trityl, 3' O-monomethoxytrityl, etc.

In another embodiment, the first and second probes of a probe pair are provided in a covalently linked form, such that the first probe is covalently linked by its 5' end to the 3' end of the second probe by a linking moiety. In one embodiment, the linking moiety comprises a chain of polynucleotides that are not significantly complementary to the target strand, the probes, or to any other nucleic acid in the sample. The linking moiety is sufficiently long to allow the target-complementary sequences in the probes to hybridize to the target strand region and to form a viable hybridization complex for cleavage. Typically, the linking moiety is longer than, preferably at least 10 nucleotides longer than, the collective length of the first and second target regions. A polynucleotide linking moiety can contain or consist of any suitable sequence. For example, the linking moiety can be a homopolymer of C, T, G or A. Alternatively, the linking moiety can contain or consist of a non-nucleotidic polymer, such as polyethylene glycol, a polypeptide such as polyglycine, etc.

In practicing the present invention, the target polynucleotide(s) are preferably converted into single-stranded form by denaturation according to known methods, to increase the accessibility of target sequences for hybridization with the complementary probes. Typically, adequate denaturation is accomplished by heating the sample to an elevated temperature, e.g., at least 90° C. or at least 95° C., for a suitable time, usually at least several seconds to several minutes or longer if necessary, to sufficiently remove inter- and intra-strand secondary structure that might otherwise interfere with probe hybridization.

The target strand regions can then be allowed to anneal to the complementary probes under conditions effective for the first and second probes to hybridize to the first and second regions in the target strand region, respectively, forming a first hybridization complex, and for third and fourth probes of a second probe pair (if present) to hybridize to the first and second regions in the target-complementary strand, respectively, forming a second hybridization complex.

Hybridization (probe annealing) is performed under conditions which are sufficiently stringent to promote sequence specificity, yet sufficiently permissive to allow formation of stable hybrids at an acceptable rate. The temperature and length of time required for probe annealing depend upon several factors including base composition, length and concentration of the primer, and the nature of the solvent used, e.g., the concentration of cosolvents such as DMSO (dimethylsulfoxide), formamide, glycerol, and counterions such as magnesium. For example, hybridization (annealing) can be carried out at a temperature that is approximately 5 to 10° C. below the melting temperature of the probe-target hybrids in the reaction mixture, although temperatures outside this range are also contemplated. For example, even if the reaction temperature is at or above the melting temperatures of first and second probes, the probes can still transiently form a duplex with the target that can be correctly cleaved and ligated. Typically, the annealing temperature is in the range of 55° C. to 75° C.

Probes and probe pairs are provided at any concentration that provides the desired result. Each probe pair is provided in excess relative to the initial amount of target sequence, and also in excess relative to the final amount of ligated product that is expected in the reaction. Annealing is usually complete within a few seconds or a few minutes. In one embodiment, the reaction mixture is maintained at a constant temperature which is suitable for hybridization, site-specific probe cleavage, and ligation. However, it is also contemplated that the temperature for probe hybridization can be different from the temperature or temperatures used for probe cleavage and ligation, or that other temperature profiles can be used. For example, after an initial hybridization time period, the temperature can be raised to expedite the cleavage reaction or ligation reaction, depending on the characteristics of the probes and of any enzymes that are used. After a sufficient amount of time, the ligated strands can be denatured by elevated temperature as above, followed by cooling to allow the target strand regions and ligated probe products to hybridize to new probe pairs for another cycle.

It will be appreciated that due to the presence of excess probe, the target strand region and the target-complementary strand region will anneal to the corresponding complementary probe pairs rather than to each other. Also, as a result of the annealing conditions, most or all of the excess probes will hybridize to their probe complements. In other words, the first probe can hybridize to the third probe, and the second probe can hybridize to the fourth probe. Under ordinary circumstances, such probe-probe duplexes do not interfere with the remaining assay steps.

If the target strand region is initially present in the sample in single-stranded form (i.e., lacking a complementary target strand), then in the contacting step of the first cycle, a hybridization complex will form between the target strand region and one of the probe pairs (e.g., the first probe pair), while the other probe pair remains in solution. However, after the first cycle of cleavage and ligation, a target-complementary strand region (the ligation product of the first probe and the cleaved second probe) is available for annealing to the second probe pair in the next cycle.

The target sequence or sequences can be detected or quantified in any appropriate way. Target detection or quantification can be based on the presence of any species or complex that either is not present in the reaction mixture unless the target is present, or is present in an amount greater than the amount of that species that would otherwise be present in the absence of the target sequence. By way of example but not limitation, such detectable species may include:

1) A first fragment from the second probe that remains hybridized to the target strand region after cleavage of the second probe 2) A second fragment from the second probe which does not associate with the third hybridization complex, and the method further includes detecting said second fragment.

3) A first hybridization complex, a second hybridization complex, or both, which are formed by hybridization of first and second probe pairs, respectively, to complementary target strand regions (or to complementary ligated strands)

4) A third hybridization complex, a fourth hybridization complex, or both, which are formed after site-specific cleavage of the second probe of each probe pair in the complex mentioned in preceding item 3).

5) A first ligated strand, a second ligated strand (complementary to the first), or both, which result from probe ligation.

Each species can be detected based on a unique property, such as electrophoretic mobility, mass, or a particular detectable label (or detectable signal associated with such label). Methods for electrophoretic separation of nucleic acids and other species are well known, and are described, for example in the works of Ausubel (1993, and later editions) and Sambrook et al. (1989). The invention also contemplates the use of probes that have distinct electrophoretic mobilities due to the presence of polymer segments or other moieties that confer distinct mobilities to the detected species in sieving or non-sieving media, as taught in U.S. Pat. Nos. 5,470,705, 5,514,543, and 5,580,732 (Grossman et al.), for example.

In one embodiment, to facilitate detection, at least one probe contains a label. Any suitable label can be used. Labels may be direct labels which themselves are detectable or indirect labels which are detectable in combination with other agents. Exemplary direct labels include but are not limited to fluorophores, chromophores, radioisotopes (e.g., $^{32}P$, $^{35}S$, $^{3}H$), spin-labels, chemiluminescent labels, and the like. Exemplary indirect labels include enzymes which catalyze a signal-producing event, and ligands such as an antigen or biotin which can bind specifically with high affinity to a detectable anti-ligand, such as a labeled antibody or avidin. Many comprehensive reviews of methodologies for labeling DNA provide guidance applicable to the present invention. Such reviews include Matthews et al. (1988); Haugland (1992), Keller and Manak (1993); Eckstein (1991); Kricka (1992), and the like. Additional methods for creating labeled nucleotides are described in Fung et al.; Hobbs et al., Menchen et al., and Bergot et al., and Rosenblum et al. (all supra).

In a preferred embodiment, the second probe in at least one probe pair contains both (1) a fluorescent dye and (2) a quencher dye that quenches at least a portion of the fluorescent dye when both dyes are present in the probe. The two dyes are positioned in the second probe so that they are separated by the linkage that is to be specifically cleaved in the cleavage step. Cleavage of the second probe results in a first fragment which contains most or all of the target-complementary sequence of the probe (and which remains hybridized to the target strand region), and a second fragment that diffuses from the hybridization complex. Separation of the fluorescent dye and the quencher dye by diffusion leads to an increased fluorescent signal from the fluorescent dye. Methods for preparing suitable probes containing fluorescer/quencher pairs can be found in Livak et al. (1995) and U.S. Pat. No. 5,876,930 (Livak et al.), for example. Quenchers are also available from various commercial sources, such as Epoch Biosciences.

In another embodiment, a first probe in a probe pair can contain a donor moiety, and a second probe can contain an acceptor moiety, so that upon ligation, the donor moiety and acceptor moiety are brought into close proximity so that fluorescence emission of the acceptor moiety is increased.

In another embodiment, a first probe in a probe pair can contain a fluorescer moiety, and a second probe can contain a quencher moiety, so that upon ligation, fluorescence emission from the fluorescer moiety decreases due to quenching.

One or more probes may also contain a member of a specific binding pair. "Specific binding pair" refers to a pair of molecules that specifically bind to one another to form a binding complex. Examples of specific binding pairs include, but are not limited to antibody-antigen (or hapten) pairs, ligand-receptor pairs, enzyme-substrate pairs, biotin-avidin pairs, complementary polynucleotide pairs, and the like. The use of a binding pair can be used to attach various labels to the probe, as discussed above, or to capture the probe on a solid support that is coated with the other member of the binding pair.

In yet another embodiment, ligation is detected or quantified using an intercalating dye such as ethidium bromide or SYBR GREEN (Molecular Probes) or a minor groove binder such as Hoechst 33258, for example, which are compounds that exhibit increased fluorescence in proportion to the amount of double-stranded nucleic acid in a sample.

Multiple Targets; Arrays

The present invention can be used to detect a plurality of different target sequences in a single sample or in a plurality of samples. In one embodiment, different target sequences are detected separately in separate reaction mixtures. In another embodiment, a sample can be contacted with a plurality of probe sets which are each designed to detect a different target sequence that may be present in the sample. The various target sequences can be detected based on detectable characteristics that are unique for each probe pair, such as mass, electrophoretic mobility, fluorescence signal, or a combination thereof. Methods of electrophoresis are well known and are described, for example, in Ausubel, Sambrook et al. (1989), and Grossman and Colburn (1992). The number of target sequences, and corresponding probe pairs, that can be used in a single reaction is a matter of choice by the user, and will depend in part on the resolvability of the properties that are used to distinguish the various reaction products.

In one embodiment, one of the first probe and second probe of a probe pair contains a distinct polynucleotide tag (a tag having a defined polynucleotide sequence) that identifies that probe pair. The tag can be directly attached to the distal end of the target-complementary sequence of a probe, or optionally can be linked to the probe by an intervening spacer group. In another embodiment, the tag is linked to an internal site within the target-complementary sequence of the probe. Thus, the tag can be linked to an intersubunit linking group, or to a nucleotide base, within a probe. For example, each tag can be attached to the 5' end of the first probe in each different probe pair, or to the 3' end of the second probe in each different probe pair.

Tagged probes or tagged probe fragments can be separated from each other by hybridization to corresponding tag complements which are immobilized on distinct solid support regions. Preferably, the solid support regions are configured as an addressable array. By "addressable array" is meant that the identity of each probe or probe fragment is known or can be determined from the position of hybridization of that probe or probe fragment on the array. Preferably, the tag complements are immobilized in discrete regions on a planar surface, such that each discrete region contains only tag complements having a particular sequence, and such that the sequence of the tag complement at each different discrete region is known. Conveniently, the tag complements are distributed as a periodic two-dimensional array of discrete tag complement regions which can be indexed via X and Y coordinates, or any equivalent thereof.

Solid phase supports can be formed using any material that allows for the tag segments to hybridize specifically to their complementary tag complements on the support. Exemplary support materials include glass; quartz; silicon; polycarbonate; metallic materials such as GaAs, copper, or germanium; a polymerized gel, such as crosslinked polyacrylamide; or membranes such as nylon, polyvinylidine difluoride (PVDF), or poly-tetrafluoroethylene.

Immobilization of tag-complements in the array is accomplished using any of a variety of suitable methods. In one approach, the tag complements are deposited onto a solid phase surface using liquid dispensing methods. For example, deposition can be accomplished robotically on a poly-lysine-coated microscope slide, followed by treatment with succinic anhydride to couple the tag complements to the polylysine moieties, as described by Schena et al. (1995) and Shalon (1995). For covalent attachment, the tag-complements may include a suitably reactive functionality for covalent attachment to the support. Exemplary linking chemistries are disclosed in Barany et al. (1991), Pon et al. (1988), and Menchen et al. (1994).

In another approach, tag complements can be synthesized on a support by photolithographic methods, as described in Fodor et al. (1991, 1995), Pirrung et al. (supra), and Shoemaker (1997). Photoremovable groups are attached to a substrate surface, and light-impermeable masks are used to control the addition of monomers to selected regions of the substrate surface by activating light-exposed regions. Monomer addition to the growing polymer chains is continued using different mask arrangements until the desired, different sequence tag complements are formed at the desired addressable locations. The masking method of Fodor et al. may also be modified to accommodate block-polymer synthesis. For example, an array of linker groups (e.g., a polypeptide, or an N-protected aminocaproic acid linked to an aminopropyl group) can be formed on the substrate surface via simultaneous activation of all immobilization regions to form a "carpet" of linker groups. The tag complements are then individually deposited on (or adsorbed to) the substrate surface as liquid drops at selected addressable locations, and are exposed to light or heat as appropriate to couple the binding moieties to the immobilized linker groups, preferably while a sufficient amount of solvent still remains from each drop.

Alternatively, the tag complements may be immobilized on the support(s) non-covalently, e.g., using ligand-receptor type interactions. For example, the tag complements may contain covalently attached biotin groups as linker groups, for binding to avidin or streptavidin polypeptides which have been attached to a support (e.g., Barrett, 1996).

Linker segments may also be included between the tag complement sequence and the support to provide a spacer arm which allows the tag-specific binding region to separate from the support, rendering the binding region more accessible to the sample. Exemplary linker groups are described, for example, in Fodor et al. (1995) and Brenner (PCT Publications cited above). Preferably, the tag complement is separated from the support by a chain comprising at least 10 chain atoms.

The support may include depressions in the support for holding the deposited tag complements. Elevated protrusions can also be used, onto which the tag complements are deposited. In yet another approach, tag complements can be formed on beads as described in U.S. Pat. No. 5,846,719 (Brenner et al.), for example. Alternatively, tag complements are attached to an array of individual beads attached to a surface, via magnetic force if the beads are magnetic (Albretsen, 1990), or with an adhesive.

In another approach, an array is formed on a substrate, such as a glass plate, which is covered with a rectangular array of pieces of polyacrylamide gel (e.g., Khrapko et al., 1991). A different tag complements is deposited at a selected site and is bound thereto by reacting a 3'-terminal dialdehyde on the tag complements with hydrazide groups on the polyacrylamide gel piece. Tag complement arrays in accordance with the invention may also be formed by robotic deposition of tag complements onto nylon (Khrapko et al., supra). Following deposition, immobilization of the tag complements may be facilitated by heat or photoactivation as appropriate.

To reduce the amounts of assay reagents used for tag detection, arrays may be formed as microarrays having tag complement region densities of greater than 100 regions/$cm^2$, 300 regions/$cm^2$, $10^3$ regions/$cm^2$, $3 \times 10^3$ regions/$cm^2$, $10^4$ regions/$cm^2$, $10^5$ regions/$cm^2$, or $10^6$ regions/$cm^2$. In addition, the number of different sequence tag complements in each array is preferably equal to or greater than 10, 20, 50, 100, 200, 500, 1000, 3000, 10,000, 30,000, 100,000, or 300,000.

The tags and tag complements may be single or double stranded, such that sequence specific hybridization forms either duplexes by Watson and Crick base-pairing, or triplexes by forward or reverse Hoogsteen bonding. In embodiments where specific hybridization occurs via triplex formation, coding of tag sequences follows the same principles as for duplex-forming tags. However, there are further constraints on the selection of word sequences. Generally, third strand association via Hoogsteen type of binding is most stable along homopyrimidine-homopurine tracks in a double stranded target. Usually, base triplets form in T-A*T or C-G*C motifs (where "-" indicates Watson-Crick pairing and "*" indicates Hoogsteen type of binding); however, other motifs are also possible. For example, Hoogsteen base pairing permits parallel and antiparallel orientations between the third strand (the Hoogsteen strand) and the purine-rich strand of the duplex to which the third strand binds, depending on conditions and the composition of the strands. Furthermore, the invention also contemplates the use of non-standard base pairing moieties such as disclosed in U.S. Pat. No. 5,432,272 (Benner) and which are available from Erogen as the "AEGIS" system.

There is extensive guidance in the literature for selecting appropriate sequences, orientation, conditions, nucleoside type (e.g. whether ribose or deoxyribose nucleosides are employed), base modifications (e.g. methylated cytosine, and the like in order to maximize, or otherwise regulate, triplex stability as desired in particular embodiments, e.g., Brenner (supra). More generally, conditions for annealing single-stranded or duplex tags to single-stranded or duplex sequence complements are well known, e.g. Brenner (supra), Ji et al. (1993), Cantor et al. (supra), Wetmur (1991), Breslauer et al. (1986), Schena (1995), and the like.

Detection

Any detection method may be used which is suitable for the type of label employed. Thus, exemplary detection methods include radioactive detection, optical absorbance detection, e.g., UV-visible absorbance detection, optical emission detection, e.g., fluorescence or chemiluminescence. For example, captured tagged species can be detected on an array by scanning all or portions of each array simultaneously or serially, depending on the scanning method used. For fluorescence labeling, selected regions on an array may be serially scanned one-by-one or row-by-row using a fluorescence microscope apparatus, such as described in Fodor (1995) and Mathies et al. (1992). Hybridization patterns may also be scanned using a CCD camera (e.g., Model TE/CCD512SF, Princeton Instruments, Trenton, N.J.) with suitable optics (Ploem, 1993), such as described in Yershov et al. (1996), or may be imaged by TV monitoring (Khrapko, 1991). For radioactive signals (e.g., $^{32}P$), a phosphorimager device can be used (Johnston et al., 1990; Drmanac et al., 1992; 1993). Other commercial suppliers of imaging instruments include General Scanning Inc., (Watertown, Mass., www.genscan.com), Genix Technologies (Waterloo, Ontario, Canada; www.confocal.com), and Applied Precision Inc. Such detection methods are particularly useful to achieve simultaneous scanning of multiple tag complement regions.

Measured signals can be analyzed manually or by appropriate computer methods to tabulate results. The results can be measured to provide qualitative or quantitative results, depending on the needs of the user. Reaction conditions can include appropriate controls for verifying the integrity of hybridization, and for providing standard curves for quantitation, if desired.

Kits

The invention also contemplates kits which are useful in practicing the invention. Such kits may include one or more probe pairs as discussed above, and optionally, a 5' nuclease enzyme and a ligase enzyme. The kit may also include buffers and any other reagents that facilitate the method.

From the foregoing, it can be seen how the features and benefits of the invention can be achieved. The invention provides a convenient method for determining the presence or absence of one or more target sequences, and for quantification as well. The method is amenable to high-throughput processing of many target sequences and many different samples. The invention can be used for a variety of purposes, such as genetic screening, allele determination, sample identification, disease diagnosis, forensics, agricultural analysis, and many others. The method can also be used to establish a sequence profile of one or more samples, for identifying or distinguishing samples.

The invention is further illustrated by way of certain examples which are not intended to limit the invention in any way.

EXAMPLE 1

Afu FEN was obtained from Third Wave Technology (Madison, Wis.). AMPLIGASE™ was purchased from Epicentre Technologies. Reaction buffer (1×) contained 10 mM MOPS pH 7.5, 10 µM NAD⁺, 3.0 mM $MgCl_2$, 0.05% NP-40, 0.05% TWEEN-20 (v:v), and 60 nM ROX passive reference (Applied Biosystems).

Genomic DNA that was homozygous for the A allele of human ligase I (from Raji leukemia cells) was obtained from PE Biosystems (DNA Template Reagent, Part No. 401970). Genomic DNA that was homozygous for the C allele of human ligase I, or heterozygous for the A and C alleles, was obtained from Coriell Institute for Medical Research.

Probe sets (see below) were prepared for detecting the following target sequences:

Target 1: HumanApoB

5'-AAGAAATTATCTCGGTCCTCACAATAAACTGC
   GAGGTCACTGTGAGTTTTCCT-3' (SEQ ID NO:1)

Target 2: Human Ligase I (A allele)

5'-AAAGCCTCACAGAGGCTGAAGTGGC
   AACAGAGAAGGAAGGAGAAGACGGGG-3'
   (SEQ ID NO:2)

Target 3: Human Ligase I (C allele)

5'-AAAGCCTCACAGAGGCTGAAGTGGC
   CACAGAGAAGGAAGGAGAAGACGGGG-3'
   (SEQ ID NO:3)

The following probe sets were synthesized by the phosphoramidite synthesis method, where F=6-Fam, and Q=Tamra, and all probe sequences are 5' to 3' (see Mullah et al., Nucl. Acids Res. 26:1026–1031 (1998); and "Chemical methods for 5' non-isotopic labelling of PCR probes and primers" (Chapter 3) by Alex Andrus, in *PCR 2: A Practical Approach*, M. J. McPherson et al., eds, IRL Press, NY (1995)):

ApoB Probe Set (control):

ApoB probe 1: AAGAAATTATCTCGGTCCTCA-CAATAAAC (SEQ ID NO:4)

ApoB probe 2: F-ACTGCGAGGTCACTGTGAGTTTTC-Q (SEQ ID NO:5)

ApoB probe 3: AAGAAAACTCACAGTGACCTCG-CAG (SEQ ID NO:6)

ApoB probe 4: F-AGTTTATTGTGAGGACCGAGATAATTTC-Q (SEQ ID NO:7)

A-Allele of Human Ligase (AHL) Probe Set:

AHL probe 1: AACCTCACAGAGGCTGAAGTGGCA (SEQ ID NO:8)

AHL probe 2: F-AAACAGAGAAGGAAGGAGAAGACGG-Q (SEQ ID NO:9)

AHL probe 3: AACCGTCTTCTCCTTCCTTCTCTGTT (SEQ ID NO:10)

AHL probe 4: F-ATGCCACTTCAGCCTCTGTGAGG-Q (SEQ ID NO:11)

C-allele of human ligase (CHL) probe set:

CHL probe 1: CCCCTCACAGAGGCTGAAGTGGCC (SEQ ID NO:12)

CHL probe 2: F-ACACAGAGAAGGAAGGAGAAGACGG-Q (SEQ ID NO:13)

CHL probe 3: CCCCGTCT TCTCCTTCCTTCTCTGTG (SEQ ID NO:14)

CHL probe 4: F-AGGCCACTTCAGCCTCTGTGAGG-Q (SEQ ID NO:15)

Alignments of the probes with corresponding target sequences are shown below. Only one target strand region is shown for each target sequence, for which probes 3 and 4 from each probe set are complementary. Probes 1 and 2 from each probe set are complementary to the complement (not shown) of the target strand region. The A base and C base that distinguish the A and C alleles, respectively, of the human ligase I gene are highlighted by bold and underlining. Double underlining indicates bases at the 3' termini of the first and third probes that are invasive with respect to same-sequence bases at or near the 5' terminal ends of the second and fourth probes, respectively. Lower case letters indicate bases which are non-complementary with respect to the target sequence (or the complement of the target).

ApoB Alignment

ApoP1: 5'-AAGAAATTATCTCGGTCCTCACAATAA
   AC-3'(SEQ ID NO:4)

ApoP2 5'-F-ACTGCGAGGTCACTGTGAGTTTTC-Q-3'(SEQ ID NO:5)

ApoTgt: AAGAAATTATCTCGGTCCTCA-CAATAAACTG
   CGAGGTCACTGTGAGTTTTCCT-3'(SEQ ID NO:1)

ApoP3: 3'-GACGCTCCAGTGACACTCAAAAGaA-5' (SEQ ID NO:6)

ApoP4: 5'-Q-CTTTAATAGAGCCAGGAGTGTTATTTGA-F-5' (SEQ ID NO:7)

AHL Alignment

AHLp1: 5'-AaCCTCACAGAGGCTGAAGTGGCA-3'(SEQ ID NO:8)

AHLp2: 5'-F-aAACAGAGAAGGAAGGAGAAGACGG-Q-3'(SEQ ID NO:9)

AHLTgt: AAAGCCTCACAGAGGCTGAAGTGGC
   AACAGAGAAGGAAGGAGAAGACGGGG-3'(SEQ ID NO:2)

AHLp3: 3'-TTGTCTCTTCCTTCCTCTTCTGCCaa-5'(SEQ ID NO:10)

AHLp4: 3'-Q-GGAGTGTCTCCGACTTCACCGTa-F-5' (SEQ ID NO:11)

CHL Alignment

CHLp1: 5-cCCCTCACAGAGGCTGAAGTGGC C-3'(SEQ ID NO:12)

CHLp2: 5'-F-aCACAGAGAAGGAAGGAGAAGACGG-Q-3'(SEQ ID NO:13)

CHLTgt: AAAGCCTCACAGAGGCTGAAGTGGC CACAGAGAAGGAAGGAGAAGACGGGG-3'(SEQ ID NO:3)

CHLp3: 3'-GTGTCTCTTCCTTCCTCTTCTGCCCC-5'(SEQ ID NO:14)

CHLp4: 3'-Q-GGAGTGTCTCCGACTTCACCGGa-F-5' (SEQ ID NO:15)

Reaction mixtures (30 μL each) were prepared containing approximately 1 to 3 ng of genomic DNA, 100 nM of each probe from the ApoB, AHL, or CHL probe set, 1 ng of Afu FEN, and 5 units of AMPLIGASE™ in 1×reaction buffer. Reaction tubes were placed in a 96 well optical plate (Part No. N801-0560) of a PE Biosystems GENEAMP™ System 7700. After heating to 95° C. for 2 min., the reaction mixtures were subjected to 50 two-step heating cycles of 65° C for 1 min. and 95° C. for 15 sec. For each well, spectra were collected within a wavelength window of 500 to 650 nm during each data collection cycle. Each data collection cycle time lasted about 7 seconds. The spectra recorded for each well were deconvoluted to reflect the signal intensities of each individual dye, and the signal intensity for FAM at the end of each cycle was plotted as a ratio with respect to the signal intensity of ROX, as a function of cycle number. Results are shown in Table 1 below, which show calculated values for the cycle number (Ct) in which specific signal was detectable over an arbitrarily selected threshold level, such that a lower estimated Ct value indicates a higher starting target concentration.

TABLE 1

| Sample Zygosity | Probe Set in Reaction Mixture | | |
|---|---|---|---|
| | ApoB | AHL | CHL |
| None | 37.2 ± 0.4 | 35.9 ± 0.2 | 42.8 ± 1.2 |
| A/A | 32.2 ± 0.1 | 30.5 ± 0.2 | 41.0 ± 0.4 |
| A/C | 30.3 ± 0.1 | 30.2 ± 0.2 | 31.2 ± 0.1 |
| C/C | 32.5 ± 0.2 | 36.0 ± 0.4 | 32.7 ± 0.2 |

The results demonstrate that the AHL and CHL probe sets provide specific detection of each target-matched genomic sequence. Specifically, a Ct value of 30.5 was observed for the homozygous A sample in the presence of the AHL probe set, whereas the CHL probe set showed no detectable amplification through 40 cycles. Conversely, a Ct value of 32.7 was calculated for the homozygous C sample in the presence of the CHL probe set, whereas the AHL probe set showed no detectable amplification until about cycle 36. For the hetero-zygous A/C sample, detectable signals were observed at about the same cycle numbers (about 30 or 31) for the AHL and CHL probe sets, respectively, consistent with a 1:1 allelic ratio.

The late-occurring signals observed with the AHL and CHL probe sets in the presence of non-target allelic samples were significantly shallower in slope than the slopes of the signals produced by the target-matched probe sets, and were probably attributable to non-template background reactions for which signals are provided in the row of data identified as "None". For example, in the absence of genomic DNA, the AHL probe set produced a Ct value of 35.9, which is substantially the same as the Ct value of 36.0 obtained for the AHL probe set reacted with the homozygous C sample. Similarly, in the absence of genomic DNA, the CHL probe set produced a Ct value of 42.8, which is close to the Ct value of 41.0 obtained for reaction of the CHL probe set with the homozygous A sample.

The results for target-matched AHL and CHL probe sets also agreed well with data obtained with the ApoB probe set, such that the Ct values obtained for the ApoB signal were within about 2 cycles of the Ct values observed for target-matched AHL and CHL probe sets. The disparity between the ApoB Ct values and the target-matched AHL or CHL values may be attributable to different amplification efficiencies for different probe sets, and pipetting errors. In all cases, the no-sample control reactions for the different probe sets occurred in much later cycles than the Ct cycle numbers, confirming the target-specificity of the probe sets.

EXAMPLE 2

The conditions in Example 1 were repeated using different concentrations of target DNA homozygous for the C allele of human ligase I (0, 1, 10, 100, and 1000 copies, each in quadruplicate) in the presence of the CHL probe set. The results are shown below:

TABLE 2

| Target Copy Number | Ct |
|---|---|
| 0 | 43.7 ± 0.6 |
| 1 | 42.7 ± 0.8 |
| 10 | 39.8 ± 0.1 |
| 100 | 35.6 ± 0.2 |
| 1000 | 31.2 ± 0.2 |

The results show that as expected, the Ct values showed an inverse linear relationship to the log of target copy number, and fewer than 10 copies could be reliably detected.

All references cited herein are incorporated by reference as if each was separately but expressly incorporated by reference.

Although the invention has been described with reference to particular embodiments, it will be appreciated that various changes and modifications may be made without departing from the scope and spirit of the invention.

What is claimed is:

1. A method for detecting a target polynucleotide sequence, the method comprising
   (a) reacting a target polynucleotide strand region and a target-complementary strand region with a first probe pair and a second probe pair,
   the first probe pair comprising (i) a first polynucleotide probe containing a sequence that is complementary to a first target region in the target strand region and (ii) a second polynucleotide probe comprising a sequence that is complementary to a second target region in the target strand region, wherein the second region is located 5' to the first region and overlaps the first region by at least one nucleotide base, and
   the second probe pair comprising (i) a third polynucleotide probe containing a sequence that is complementary to a first region in the target-complementary strand region and (ii) a fourth polynucleotide probe containing a sequence that is complementary to a second region in the target-complementary strand region, wherein the second region is located 5' to the first region and overlaps the first region by at least one nucleotide base,
   under conditions effective for the first and second probes to hybridize to the first and second regions in the target strand region, respectively, forming a first hybridization complex, and for the third and fourth probes to hybridize to the first and second regions in the target-complementary strand region, respectively, forming a second hybridization complex,
   (b) cleaving the second probe in the first hybridization complex, and the fourth probe in the second hybridization complex, to form (i) a third hybridization complex comprising the target strand region, the first probe, and a first fragment of the second probe having a 5' terminal nucleotide located immediately contiguous to a 3' terminal nucleotide of the first probe, and (ii) a fourth hybridization complex comprising the target-complementary strand region, the third probe, and a first fragment of the fourth probe having a 5' terminal nucleotide located immediately contiguous to a 3' terminal nucleotide of the third probe,
   (c) ligating the first probe to the hybridized fragment of the second probe to form a first ligated strand hybridized to the target strand region, and ligating the third probe to the fragment of the fourth probe to form a second ligated strand hybridized to the target-complementary strand region,
   (d) denaturing the first ligated strand from the target strand region and the second ligated strand from the target-complementary strand region, and
   (e) performing one or more additional cycles of steps (a) through (d), with the proviso that in the last cycle, step (d) is optionally omitted.

2. The method of claim 1, wherein the first region overlaps the second region by one nucleotide base.

3. The method of claim 1, wherein the 5' ends of the first and third probes terminate with a group other than a nucleotide 5' phosphate group.

4. The method of claim 3, wherein the 5' ends of the first and third probes terminate with a nucleotide 5' hydroxyl group.

5. The method of claim 1, wherein the 5' ends of the second and fourth probes terminate with a group other than a nucleotide 5' phosphate group.

6. The method of claim 5, wherein the 5' ends of the second and fourth probes terminate with a nucleotide 5' hydroxyl group.

7. The method of claim 1, wherein the 5' ends of the first, second, third and fourth probes terminate with a group other than a nucleotide 5' phosphate group.

8. The method of claim 1, wherein the 3' ends of the second and fourth probes terminate with a group other than a nucleotide 3' hydroxyl group.

9. The method of claim 8, wherein said 3' ends of the second and fourth probes terminate with a nucleotide 3' phosphate group.

10. The method of claim 1, wherein at least one of the probes contains a detectable label.

11. The method of claim 10, wherein the label is a fluorescent label.

12. The method of claim 10, wherein the label is a radiolabel.

13. The method of claim 10, wherein the label is a chemiluminescent label.

14. The method of claim 10, wherein the label is an enzyme.

15. The method of claim 10, wherein at least one of the first probe and the third probe contains a detectable label.

16. The method of claim 15, wherein each of the first probe and third probe contains a detectable label.

17. The method of claim 16, wherein the detectable labels on the first probe and third probe are the same.

18. The method of claim 10, wherein at least one of the second probe and the fourth probe contains a detectable label.

19. The method of claim 18, wherein each of the second probe and the fourth probe contains a detectable label.

20. The method of claim 19, wherein the second probe and fourth probe contain the same detectable label.

21. The method of claim 1, wherein said cleaving produces a second fragment from the second probe which does not associate with the third hybridization complex, and the method further includes detecting said second fragment.

22. The method of claim 21, wherein at least one of the second probe and the fourth probe contains both (i) a fluorescent dye and (ii) a quencher dye which is capable of quenching fluorescence emission from the fluorescent dye when the fluorescent dye is subjected to fluorescence excitation energy, and said cleaving severs a covalent linkage between the fluorescent dye and the quencher dye in the second probe and/or fourth probe, thereby increasing an observable fluorescence signal from the fluorescent dye.

23. The method of claim 22, wherein the second probe and the fourth probe each contain (i) a fluorescent dye and (ii) a quencher dye.

24. The method of claim 21, wherein said cleaving further produces a second fragment from the fourth probe which does not associate with the fourth hybridization complex, and the method further includes detecting both second fragments.

25. The method of claim 21, wherein said second fragment comprises one or more contiguous nucleotides which are substantially non-complementary to the target strand region.

26. The method of claim 25, wherein said one or more contiguous nucleotides comprise 1 to 20 nucleotides.

27. The method of claim 21, which further includes immobilizing the second fragment on a solid support.

28. The method of claim 21, which further includes subjecting the second fragment to electrophoresis.

29. The method of claim 21, which further includes detecting the second fragment by mass spectrometry.

30. The method of claim 21, which comprises detecting the second fragment after the last cycle.

31. The method of claim 21, which comprises detecting the second fragment during or after a plurality of cycles.

32. The method of claim 31, which comprises detecting the second fragment during all of the cycles.

33. The method of claim 1, which further includes detecting the first hybridization complex, the second hybridization complex, or both, after at least one cycle.

34. The method of claim 1, which further includes detecting the third hybridization complex, the fourth hybridization complex, or both, after at least one cycle.

35. The method of claim 1, which further includes detecting the first ligated strand, the second ligated strand, or both, after at least one cycle.

36. The method of claim 35, wherein said detecting comprises an electrophoretic separation step.

37. The method of claim 35, wherein the first ligated strand, the second ligated strand, or both, are detected by mass spectrometry.

38. The method of claim 35, wherein the first ligated strand is detected.

39. The method of claim 38, wherein the first ligated strand contains a fluorescent label.

40. The method of claim 35, wherein the first ligated strand and second ligated strand are detected, and each ligated strand contains a detectable label.

41. The method of claim 40, wherein each detectable label is a fluorescent label.

42. The method of claim 35, wherein the first ligated strand, the second ligated strand, or both, are immobilized on a solid support.

43. The method of claim 42, wherein after the last cycle, the first ligated strand is immobilized on the solid support and detected.

44. The method of claim 42, wherein said reacting comprises providing the first probe or second probe immobilized on the solid support, so that the first ligated strand is immobilized on the solid support.

45. The method of claim 1, wherein the first probe pair comprises a first probe and a second probe in covalently linked form, such that the first probe is covalently linked by its 5' end to the 3' end of the second probe by a linking moiety.

46. The method of claim 45, wherein the second probe pair comprises a third probe and a fourth probe in covalently linked form, such that the third probe is covalently linked by its 5' end to the 3' end of the fourth probe by a linking moiety.

47. The method of claim 45, wherein the linking moiety comprises a chain of polynucleotides that is not substantially complementary to the target polynucleotide.

48. The method of claim 1, wherein said reacting further comprises providing a fifth polynucleotide probe which is complementary to a sequence variant of a region to which either the first probe, second probe, third probe, or fourth probe is complementary.

49. The method of claim 48, wherein the fifth polynucleotide probe and the first polynucleotide probe are complementary to alternative polymorphic sequences in the target polynucleotide strand region.

50. The method of claim 49, wherein the target complementary sequences of the fifth polynucleotide probe and the first polynucleotide probe contain different 3' terminal nucleotides that are complementary to alternative target nucleotide bases in the alternative polymorphic sequences.

51. The method of claim 49, wherein the first polynucleotide probe contains a first detectable label, and the fifth polynucleotide probe contains a second detectable label that is distinguishable from the first detectable label.

52. The method of claim 51, wherein said labels are fluorescent labels.

53. The method of claim 48, wherein the fifth polynucleotide probe and the second polynucleotide probe are complementary to alternative polymorphic sequences in the target polynucleotide strand region.

54. The method of claim 53, wherein the target complementary sequences of the fifth polynucleotide probe and of the second polynucleotide probe contain different 5' terminal nucleotides that are complementary to alternative target nucleotide bases in the alternative polymorphic sequences.

55. The method of claim 53, wherein the second polynucleotide probe contains a first detectable label, and the fifth polynucleotide probe contains a second detectable label that is distinguishable from the first detectable label.

56. The method of claim 55, wherein said labels are fluorescent labels.

57. The method of claim 1, wherein the 5' terminal base of said first region of the target strand region abuts the 5' terminal base of said first region of the target-complementary strand region.

58. The method of claim 1, wherein the 5' terminal base of said first region of the target strand region is separated from the 5' terminal base of said first region of the target-complementary strand region by at least one nucleotide base.

59. The method of claim 1, wherein said reacting further includes providing a third probe pair which is complementary to a second target polynucleotide strand region and a fourth probe pair which is complementary to a complement of the second target polynucleotide strand region, the third probe pair comprising (i) a fifth polynucleotide probe containing a sequence that is complementary to a first target region in the second target strand region and (ii) a sixth polynucleotide probe comprising a sequence that is complementary to a second target region in the second target strand region, wherein the second region is located 5' to the first region and overlaps the first region by at least one nucleotide base, and the fourth probe pair comprising (i) a seventh polynucleotide probe containing a sequence that is complementary to a first region in the second said target-complementary strand region and (ii) an eighth polynucleotide probe containing a sequence that is complementary to a second region in the second said target-complementary strand region, wherein the second region is located 5' to the first region and overlaps the first region by at least one nucleotide base, under conditions effective for the fifth and sixth probes to hybridize to the first and second regions in the second target strand region, respectively, forming a fifth hybridization complex, and for the seventh and eighth probes to hybridize to the first and second regions in the second said target-complementary strand region, respectively, forming a sixth hybridization complex if the second said target-complementary strand region is present in the sample.

60. The method of claim 1, wherein the first probe pair and the second probe pair taken together constitute a first probe set, and the method further comprises reacting a sample with a plurality of different probe sets which are each designed to detect a different target polynucleotide sequence which may be present in the sample.

61. The method of claim 60, wherein said detecting comprises detecting at least one ligated strand produced by each different probe set when the corresponding target sequence is present.

62. The method of claim 61, wherein ligated strands from different probe sets are detected by mass spectrometry.

63. The method of claim 61, wherein ligated strands from different probe sets are detected by electrophoresis.

64. The method of claim 63, wherein ligated strands from different probe sets have different electrophoretic mobilities.

65. The method of claim 64, wherein ligated strands from different probe sets contain detectable labels which may be the same or different.

66. The method of claim 65, wherein the labels are fluorescent labels.

67. The method of claim 63, wherein ligated strands from at least two different probe sets contain different fluorescent labels.

68. The method of claim 60, wherein prior to step (a), the first probe, the second probe, the third probe, or the fourth probe from the different probe sets is immobilized on a distinct solid support region.

69. The method of claim 60, wherein one of the first probe, the second probe, the third probe, or the fourth probe in each probe set contains a distinct polynucleotide tag that identifies that probe set.

70. The method of claim 69, which comprises hybridizing species containing said tags to a plurality of corresponding tag complements which are immobilized on distinct solid support regions.

71. The method of claim 70, wherein each distinct polynucleotide tag is attached to the 5' end of the first probe in each different probe set.

72. The method of claim 70, wherein each distinct polynucleotide tag is attached to the 3' end of the second probe in each different probe set.

73. The method of claim 70, wherein said distinct solid support regions are located on a substantially planar surface.

74. The method of claim 70, wherein said distinct solid support regions are located on different beads.

75. The method of claim 60, wherein for each probe set, said cleaving produces a second fragment from the second probe of the probe set which does not associate with the third hybridization complex, and the method further includes detecting the second fragment.

76. The method of claim 75, wherein second fragments from different probe sets are detected by mass spectrometry.

77. The method of claim 75, wherein second fragments from different probe sets are detected by electrophoresis.

78. The method of claim 77, wherein second fragments from different probe sets have different electrophoretic mobilities.

79. The method of claim 77, wherein second fragments from different probe sets contain detectable labels which may be the same or different.

80. The method of claim 79, wherein the labels are fluorescent labels.

81. The method of claim 75, wherein second fragments from at least two different probe sets contain different fluorescent labels.

82. The method of claim 75, wherein the second fragment from each different probe set contains a distinct polynucleotide tag that identifies the probe set.

83. The method of claim 82, which comprises hybridizing second fragments containing said tags to a plurality of corresponding tag complements which are immobilized on distinct solid support regions.

84. The method of claim 83, wherein said distinct solid support regions are located on a substantially planar surface.

85. The method of claim 83, wherein said distinct solid support regions are located on different beads.

86. A method for detecting a target polynucleotide sequence, the method comprising (a) reacting a target polynucleotide strand region with a first probe pair, the first probe pair comprising (i) a first polynucleotide probe containing a sequence that is complementary to a first target region in the target strand region and (ii) a second polynucleotide probe comprising a sequence that is complementary to a second target region in the target strand region, wherein the second region is located 5' to the first region and overlaps the first region by at least one nucleotide base, under conditions effective for the first and second probes to hybridize to the first and second regions in the target strand region, respectively, forming a first hybridization complex, (b) cleaving the second probe in the first hybridization complex to form (i) a second hybridization complex comprising the target strand region, the first probe, and a first fragment of the second probe having a 5' terminal nucleotide located immediately contiguous to a 3' terminal nucleotide of the first probe, (c) ligating the first probe to the hybridized fragment of the second probe to form a first ligated strand hybridized to the target strand region, (d) denaturing the first ligated strand from the target strand region, and (e) performing one or more additional cycles of steps (a) through (d), with the proviso that in the last cycle, step (d) is optionally omitted.

87. The method of claim 86, wherein the first region overlaps the second region by one nucleotide base.

88. The method of claim 86, wherein the 5' end of the first probe terminates with a group other than a nucleotide 5' phosphate group.

89. The method of claim 88, wherein the 5' end of the first probe terminates with a nucleotide 5' hydroxyl group.

90. The method of claim 86, wherein the 5' end of the second probe terminates with a group other than a nucleotide 5' phosphate group.

91. The method of claim 90, wherein the 5' end of the second probe terminates with a nucleotide 5' hydroxyl group.

92. The method of claim 86, wherein the 5' end of the first and second probes terminate with a group other than a nucleotide 5' phosphate group.

93. The method of claim 86, wherein the 3' end of the second probe terminates with a group other than a nucleotide 3' hydroxyl group.

94. The method of claim 93, wherein said 3' end of the second probe terminates with a nucleotide 3' phosphate group.

95. The method of claim 86, wherein at least one of the probes contains a detectable label.

96. The method of claim 95, wherein the label is a fluorescent label.

97. The method of claim 95, wherein the label is a radiolabel.

98. The method of claim 95, wherein the label is a chemiluminescent label.

99. The method of claim 95, wherein the label is an enzyme.

100. The method of claim 95, wherein the first probe contains a detectable label.

101. The method of claim 95, wherein the second probe contains a detectable label.

102. The method of claim 86, wherein said cleaving produces a second fragment from the second probe which does not associate with the second hybridization complex, and the method further includes detecting said second fragment.

103. The method of claim 102, wherein the second probe contains both (i) a fluorescent dye and (ii) a quencher dye which is capable of quenching fluorescence emission from the fluorescent dye when the fluorescent dye is subjected to fluorescence excitation energy, and said cleaving severs a covalent linkage between the fluorescent dye and the quencher dye in the second probe, thereby increasing an observable fluorescence signal from the fluorescent dye.

104. The method of claim 102, wherein said second fragment comprises one or more contiguous nucleotides which are substantially non-complementary to the target strand region.

105. The method of claim 104, wherein said one or more contiguous nucleotides comprise 1 to 20 nucleotides.

106. The method of claim 102, which further includes immobilizing the second fragment on a solid support.

107. The method of claim 102, which further includes subjecting the second fragment to electrophoresis.

108. The method of claim 102, which further includes detecting the second fragment by mass spectrometry.

109. The method of claim 102, which comprises detecting the second fragment after the last cycle.

110. The method of claim 102, which comprises detecting the second fragment during or after a plurality of cycles.

111. The method of claim 110, which comprises detecting the second fragment during all of the cycles.

112. The method of claim 86, which further includes detecting the first hybridization complex after at least one cycle.

113. The method of claim 86, which further includes detecting the second hybridization complex after at least one cycle.

114. The method of claim 86, which further includes detecting the first ligated strand after at least one cycle.

115. The method of claim 114, wherein said detecting comprises an electrophoretic separation step.

116. The method of claim 114, wherein the first ligated strand is detected by mass spectrometry.

117. The method of claim 114, wherein the first ligated strand contains a fluorescent label.

118. The method of claim 114, wherein the first ligated strand is immobilized on a solid support.

119. The method of claim 118, wherein after the last cycle, the first ligated strand is immobilized on the solid support and detected.

120. The method of claim 118, wherein said reacting comprises providing the first probe or second probe immobilized on the solid support, so that the first ligated strand is immobilized on the solid support.

121. The method of claim 86, wherein the first probe pair comprises a first probe and a second probe in covalently linked form, such that the first probe is covalently linked by its 5' end to the 3' end of the second probe by a linking moiety.

122. The method of claim 121, wherein the linking moiety comprises a chain of polynucleotides that is not substantially complementary to the target polynucleotide.

123. The method of claim 86, wherein said reacting further comprises providing a third polynucleotide probe which is complementary to a sequence variant of a region to which either the first probe or second probe is complementary.

124. The method of claim 123, wherein the third polynucleotide probe and the first polynucleotide probe are complementary to alternative polymorphic sequences in the target polynucleotide strand region.

125. The method of claim 124, wherein the target complementary sequences of the third polynucleotide probe and the first polynucleotide probe contain different 3' terminal nucleotides that are complementary to alternative target nucleotide bases in the alternative polymorphic sequences.

126. The method of claim 124, wherein the first polynucleotide probe contains a first detectable label, and the third polynucleotide probe contains a second detectable label that is distinguishable from the first detectable label.

127. The method of claim 126, wherein said labels are fluorescent labels.

128. The method of claim 123, wherein the third polynucleotide probe and the second polynucleotide probe are complementary to alternative polymorphic sequences in the target polynucleotide strand region.

129. The method of claim 128, wherein the target complementary sequences of the third polynucleotide probe and of the second polynucleotide probe contain different 5' terminal nucleotides that are complementary to alternative target nucleotide bases in the alternative polymorphic sequences.

130. The method of claim 128, wherein the second polynucleotide probe contains a first detectable label, and the third polynucleotide probe contains a second detectable label that is distinguishable from the first detectable label.

131. The method of claim 130, wherein said labels are fluorescent labels.

132. The method of claim 86, wherein the 5' terminal base of said first region of the target strand region abuts the 5' terminal base of said first region of the target-complementary strand region.

133. The method of claim 86, wherein the 5' terminal base of said first region of the target strand region is separated from the 5' terminal base of said first region of the target-complementary strand region by at least one nucleotide base.

134. The method of claim 86, wherein said reacting further includes providing a second probe pair which is complementary to a second target polynucleotide strand region, the second probe pair comprising (i) a third polynucleotide probe containing a sequence that is complementary to a first target region in the second target strand region and (ii) a fourth polynucleotide probe comprising a sequence that is complementary to a second target region in the second target strand region, wherein the second region is located 5' to the first region and overlaps the first region by at least one nucleotide base, under conditions effective for the third and fourth probes to hybridize to the first and second regions in the second target strand region, respectively, forming a third hybridization complex if the second said target-complementary strand region is present in the sample.

135. The method of claim 86, wherein the method further comprises reacting a sample with a plurality of different probe pairs which are each designed to detect a different target polynucleotide sequence which may be present in the sample.

136. The method of claim 135, wherein said detecting comprises detecting at least one ligated strand produced by each different probe pair when the corresponding target sequence is present.

137. The method of claim 136, wherein ligated strands from different probe pairs are detected by mass spectrometry.

138. The method of claim 136, wherein ligated strands from different probe pairs are detected by electrophoresis.

139. The method of claim 138, wherein ligated strands from different probe pairs have different electrophoretic mobilities.

140. The method of claim 139, wherein ligated strands from different probe pairs contain detectable labels which may be the same or different.

141. The method of claim 140, wherein the labels are fluorescent labels.

142. The method of claim 138, wherein ligated strands from at least two different probe pairs contain different fluorescent labels.

143. The method of claim 135, wherein prior to step (a), the first probe or the second probe from one or more different probe pairs is immobilized on a distinct solid support region.

144. The method of claim 135, wherein the first probe or the second probe in each probe pair contains a distinct polynucleotide tag that identifies that probe pair.

145. The method of claim 144, which comprises hybridizing species containing said tags to a plurality of corresponding tag complements which are immobilized on distinct solid support regions.

146. The method of claim 145, wherein each distinct polynucleotide tag is attached to the 5' end of the first probe in each different probe pair.

147. The method of claim 145, wherein each distinct polynucleotide tag is attached to the 3' end of the second probe in each different probe pair.

148. The method of claim 145, wherein said distinct solid support regions are located on a substantially planar surface.

149. The method of claim 145, wherein said distinct solid support regions are located on different beads.

150. The method of claim 135, wherein for each probe pair, said cleaving produces a second fragment from the second probe of the probe pair which does not associate with the third hybridization complex, and the method further includes detecting the second fragment.

151. The method of claim 150, wherein second fragments from different probe pairs are detected by mass spectrometry.

152. The method of claim 150, wherein second fragments from different probe pairs are detected by electrophoresis.

153. The method of claim 152, wherein second fragments from different probe pairs have different electrophoretic mobilities.

154. The method of claim 152, wherein second fragments from different probe pairs contain detectable labels which may be the same or different.

155. The method of claim 154, wherein the labels are fluorescent labels.

156. The method of claim 150, wherein second fragments from at least two different probe pairs contain different fluorescent labels.

157. The method of claim 150, wherein the second fragment from each different probe pair contains a distinct polynucleotide tag that identifies the probe pair.

158. The method of claim 157, which comprises hybridizing second fragments containing said tags to a plurality of corresponding tag complements which are immobilized on distinct solid support regions.

* * * * *